US011944842B2

(12) United States Patent
Murdeshwar et al.

(10) Patent No.: US 11,944,842 B2
(45) Date of Patent: Apr. 2, 2024

(54) PHOTODYNAMIC THERAPY DEVICE AND METHODS OF USE

(71) Applicant: GYRUS ACMI, INC., Southborough, MA (US)

(72) Inventors: Nikhil M. Murdeshwar, Maple Grove, MN (US); Thomas J. Holman, Princeton, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 231 days.

(21) Appl. No.: 17/125,598

(22) Filed: Dec. 17, 2020

(65) Prior Publication Data
US 2021/0187315 A1 Jun. 24, 2021

Related U.S. Application Data

(60) Provisional application No. 62/951,447, filed on Dec. 20, 2019.

(51) Int. Cl.
*A61N 5/06* (2006.01)
(52) U.S. Cl.
CPC ........... *A61N 5/062* (2013.01); *A61N 5/0603* (2013.01); *A61N 2005/0611* (2013.01)
(58) Field of Classification Search
CPC .................. A61N 5/062; A61N 5/0603; A61N 2005/0611; A61N 2005/063;
(Continued)

(56) References Cited

U.S. PATENT DOCUMENTS

| 5,527,308 A * | 6/1996 | Anderson | A61N 5/062 606/17 |
| 6,058,937 A * | 5/2000 | Doiron | A61N 5/062 514/185 |

(Continued)

FOREIGN PATENT DOCUMENTS

| CN | 112999522 A | 6/2021 | |
| EP | 3838342 B1 | 10/2023 | |
| WO | WO-2004012805 A2 * | 2/2004 | ........... A61B 18/245 |

OTHER PUBLICATIONS

"Shishkova, et al., Photodynamic Therapy for Gynecological Diseases and Breast Cancer, 2012, Cancer Bio Med 2012, 9-17" (Year: 2012).*

(Continued)

*Primary Examiner* — Joseph M Dietrich
*Assistant Examiner* — Michael T. Holtzclaw
(74) *Attorney, Agent, or Firm* — Schwegman Lundberg & Woessner, P.A.

(57) ABSTRACT

A therapy device comprises a shaft extending between proximal and distal portions, a surgical instrument located at the distal portion, a handpiece located at the proximal portion, a treatment end located at the distal end of the surgical instrument that can apply photodynamic therapy (PDT). The treatment end includes an applicator to apply a photosensitizer to a surface of a target tissue and a light emitter that can emit generated phototherapeutic light to activate the photosensitizer to ablate target tissue. A method for providing PDT to the target tissue includes inserting the therapy device into the patent, applying the photosensitizer and phototherapeutic light to a surface of the target tissue, and removing the device from the patient.

25 Claims, 11 Drawing Sheets

(58) Field of Classification Search
CPC .... A61N 2005/0643; A61N 2005/0644; A61B 2018/00196; A61B 2018/00559
See application file for complete search history.

(56) References Cited

U.S. PATENT DOCUMENTS

| | | | | |
|---|---|---|---|---|
| 10,874,875 | B2* | 12/2020 | Klem | .................. A61P 35/00 |
| 11,020,175 | B2* | 6/2021 | Sharma | ................ A61M 25/10 |
| 2003/0028227 | A1 | 2/2003 | Neuberger et al. | |
| 2003/0130575 | A1* | 7/2003 | Desai | .................. A61K 9/0034 |
| | | | | 600/417 |
| 2004/0193235 | A1 | 9/2004 | Altshuler et al. | |
| 2006/0167531 | A1* | 7/2006 | Gertner | ................ A61N 5/0603 |
| | | | | 607/86 |
| 2008/0245371 | A1 | 10/2008 | Gruber | |
| 2010/0305494 | A1* | 12/2010 | Clements | ............. A61N 5/0624 |
| | | | | 422/243 |
| 2011/0040170 | A1 | 2/2011 | Geva et al. | |
| 2011/0190689 | A1 | 8/2011 | Bennett et al. | |
| 2012/0197245 | A1* | 8/2012 | Burnett | ........... A61B 17/12022 |
| | | | | 606/21 |
| 2012/0245581 | A1* | 9/2012 | Truckai | .............. A61B 18/1485 |
| | | | | 606/41 |
| 2013/0274549 | A1 | 10/2013 | Natale et al. | |
| 2014/0188035 | A1* | 7/2014 | Ehrenreich | ............ A61N 5/062 |
| | | | | 604/21 |
| 2016/0015259 | A1* | 1/2016 | Mody | .................. A61B 8/0841 |
| | | | | 600/106 |
| 2017/0143947 | A1 | 5/2017 | Coulson et al. | |
| 2017/0246472 | A1* | 8/2017 | Chen | ................. A61M 37/0092 |
| 2021/0052914 | A1* | 2/2021 | Yoshino | ............... A61N 5/0603 |
| 2022/0153714 | A1* | 5/2022 | Vendrell | ............... C07D 293/12 |

OTHER PUBLICATIONS

"Bown, Scientists and Clinicians create a bright future for photodynamic therapy (PDT), 2004, IEEE" (Year: 2004).*
"European Application Serial No. 20215847.3, Extended European Search Report dated May 11, 2021", 13 pgs.
"European Application Serial No. 20215847.3, Response filed Dec. 21, 2021 to Extended European Search Report dated May 11, 2021", 9 pgs.

* cited by examiner

PHOTODYNAMIC THERAPY DEVICE AND METHODS OF USE

PRIORITY CLAIM

This application claims priority to U.S. Ser. No. 62/951,447, filed on Dec. 20, 2019, entitled "PHOTODYNAMIC THERAPY DEVICE AND METHODS OF USE", the disclosure of which is incorporated by reference in its entirety.

TECHNICAL FIELD

This document pertains generally, but not by way of limitation, to surgical instruments and methods that include surgical tooling that can be used to apply photodynamic therapy to treat target tissue.

BACKGROUND

Many surgical procedures involve the treatment or removal of target tissue, e.g., diseased or unwanted tissue, located inside of a patient. As such, these procedures require access to the internal anatomy of the patient via an open procedure or through a smaller opening in minimally invasive procedures.

Women suffer from a variety of uterine abnormalities that can cause various issues. Endometriosis is a condition in which tissue that normally lines the inside of the uterus, the endometrium, grows outside the uterus. Endometriosis can cause severe, ongoing chronic pain. Often, endometriosis occurs in and around the pelvis, such as near the ovaries, fallopian tubes, and other tissue lining the pelvis. In rare cases, endometrial tissue can spread beyond pelvic organs. Endometriosis can include shallow endometrial tissue growth in and around these areas, deeper endometrial tissue growth, or both.

Another abnormality is menorrhagia, which refers to menstrual bleeding lasting more than seven days at a time, and can often include heavy bleeding. Menorrhagia affects more than ten million American women every year, meaning about one out of every five women nationally has menorrhagia. Untreated menorrhagia can cause anemia, a common blood problem in which the patient lacks sufficient healthy red blood cells to carry adequate oxygen throughout the body.

Menorrhagia can be caused by uterine problems, hormonal problems, or other illnesses. Some particular causes can include, but are not limited to, growths or tumors in the uterus, cancer of the uterus or cervix, pregnancy-related problems such as miscarriage or ectopic pregnancy, bleeding disorders, some types of birth control, kidney, thyroid, or liver diseases, infection of the female reproduction organs such as pelvic inflammatory disease, menopause, child birth, fibroids or polyps in the lining or muscles of the uterus, taking certain drugs such as aspirin, or combinations thereof.

OVERVIEW

A variety of approaches can be taken for treatment of uterine abnormalities including endometriosis, menorrhagia, polyps, and fibroids. For example, ablation therapy can be provided to treat cases various uterine abnormalities. In an example of treating endometriosis, targeted ablation such as radiofrequency (RF) ablation can be used to provide electromagnetic energy for ablating tissue or can provide a blade-like device for physically excising tissue. In an example of treating menorrhagia, the endometrial tissue in the uterus can be treated by ablation therapy so that the tissue does not continue to heavily bleed during the menstrual cycle. Such treatment of the uterus can be referred to as global endometrial ablation (GEA). GEA approaches can use a variety of ablation technologies to ablate the endometrium and prevent menorrhagia. Some of these approaches can include radiofrequency (RF) energy, microwave energy, cryogenics, thermal energy, steam, and plasma ablation technologies. Devices and methods for delivery of these approaches can be large and can create patient pain or discomfort when used.

To help increase efficacy and reduce complications, the present disclosure describes, among other things, an improved treatment modality using photodynamic therapy to treat various uterine abnormalities. Photodynamic Therapy (PDT), is the treatment of diseased, usually hyper proliferative tissue using photosensitizing chemicals and light. For example, PDT involves two non-toxic components that are combined at the treatment site to induce cellular and tissue damage in an oxygen-dependent manner. A non-toxic photosensitizer drug and a non-hazardous light of a matched wavelength are delivered to the treatment site. The photosensitization of the drug elicits the transfer of energy or an electron to molecular oxygen resulting in instant local generation of cytotoxic reactive oxygen species (ROS). Depending on the drug and the treatment protocol, phototoxicity can be directed toward the targeted tissue. The half-life of these radicals in the biological milieu is extremely short, thereby confining the damage to the illuminated area. Compared to surgical resection of tissue and ablations therapy, PDT is a highly controlled, minimally-invasive, local treatment that can effectively treat uterine abnormalities such as endometriosis, menorrhagia, and polyps, among others.

An example of previous PDT procedures includes treating tumors. Typically, the photosensitizer is delivered, generally intravenously, then waiting for some period of time for the photosensitizer to be accumulated within the target tissues while most nontarget tissue eliminates the photosensitizer. The therapeutic response of PDT includes both cellular and vascular effects. Current therapy protocols for PDT require the procedural step of allowing a period of time to elapse after injection of a photosensitizer into the blood stream to permit the photosensitizers to sufficiently accumulate in a target tissue, sometimes referred to as "drug-to-light" time. The countdown, the elapsed time required for accumulation prior to administering phototherapeutic light, begins upon introduction of the photodynamically active photosensitizer into the patient's circulatory system. With time, the photosensitizer is taken up by tissue(s) and tissue components and bound thereto. While utilization of this preferential, differentially selective photosensitizer uptake/retention by hyper-proliferating tissue is effective for a variety of photosensitizers and target tissues, due to uptake throughout the body and elimination, the delay time necessary for the accumulation of a therapeutically effective concentration of photosensitizer in the tissue generally requires the use of a relatively high photosensitizer dose. This high level of drug, in turn, can lead to problems such as systemic and local toxicity and prolonged photosensitivity of the skin. In addition, this methodology does not specifically target vasculature but focuses instead on the selective ability of a target tissue (a tissue to be treated by PDT), to take up and retain photosensitizers from the blood. Additionally, by injecting the photosensitizer into the patient's circulatory system and waiting until a sufficient amount is retained within the target tissue, provides a critical window in which the illumination needs to happen for efficient treatment of the target tissue.

The present disclosure describes devices and methods that can deliver selective targeted PDT therapy to treat various conditions and eliminate the requirement of previous approaches needing to wait between the injection of the photosensitizer and illumination. Further, the devices and methods disclosed herein can provide either a targeted PDT treatment for a specific target tissue (e.g., endometriosis or polyp) or can provide a global PDT treatment that can be used to treat, e.g., the intra-uterine wall for menorrhagia.

In particular, the devices and methods disclosed herein provide delivery of the photosensitizer and illumination to a surface of a target tissue. In an example, the photosensitizer and the illumination occur substantially simultaneously. In doing so, precise targeted PDT therapy can be delivered to the target tissue. Such an approach can include providing or using a PDT therapy device for producing intra-uterine tissue effects for menorrhagia and targeted tissue effects for endometriosis and uterine polyps. The therapy device can include a portion that can be sized and shaped for at least partial insertion into a patient. The device can have a shaft, including a proximal portion and a distal portion. The device can further include a treatment end that includes a therapy light emitter and an applicator that can deliver the photosensitizer in a desired manner to a particular tissue or area (target tissue). The photosensitizer and therapy light can be delivered to the tissue or area simultaneously or substantially simultaneously so that the tissue or area can be effectively treated. Further, since the photosensitizer is being applied to the surface of the tissue, the amount of the photosensitizer used and absorbed by the body can be reduced and the uncertain waiting in previous approaches to allow a sufficient amount to be concentrated in a particular tissue is eliminated.

This overview is intended to provide an overview of subject matter of the present patent application. It is not intended to provide an exclusive or exhaustive explanation of the invention. The detailed description is included to provide further information about the present patent application.

Figure 1:
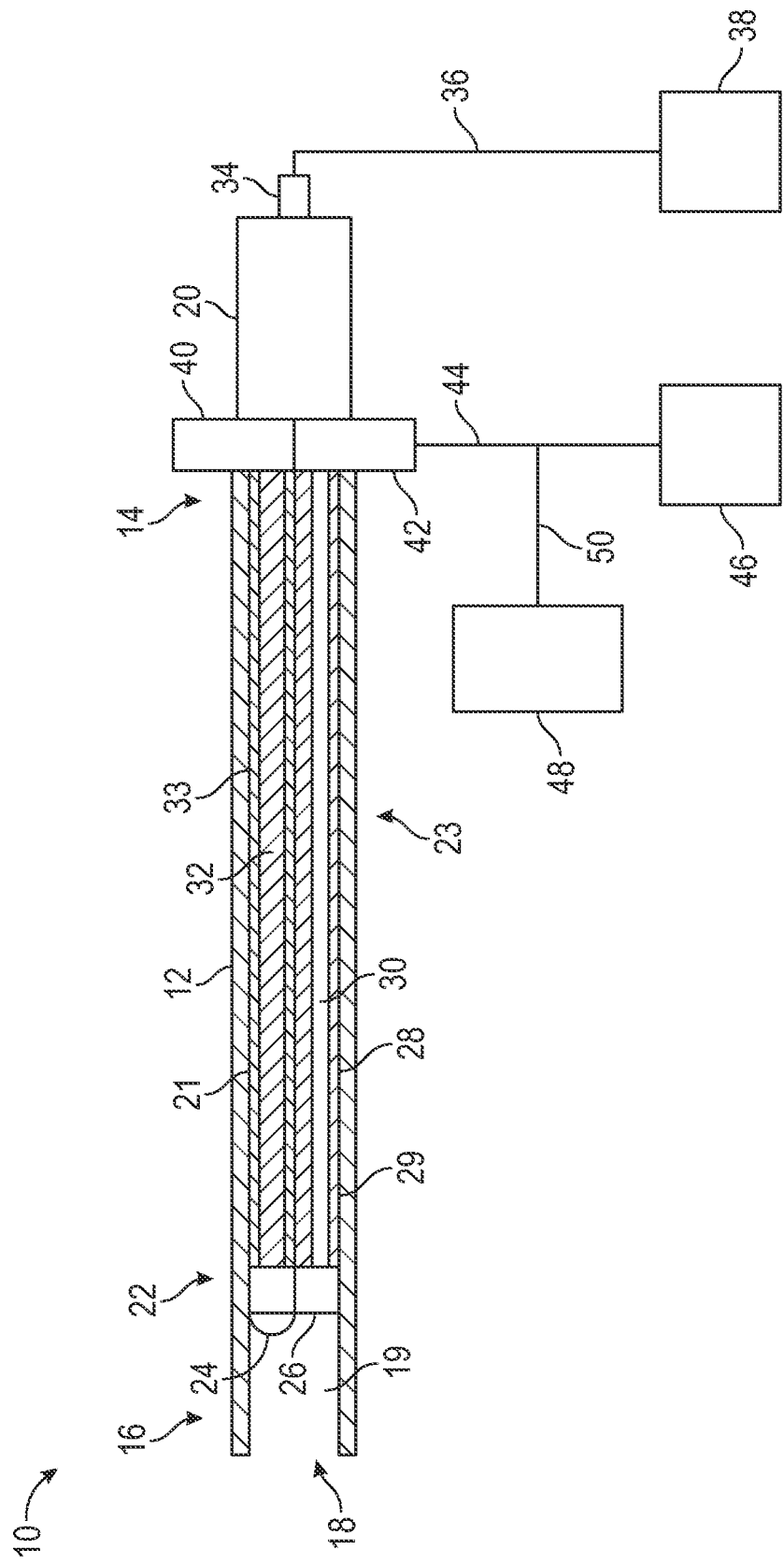
FIG. 1 is a schematic illustration of a therapy device including a surgical device having a treatment end that can provide PDT to a target tissue, according to one example of the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure describes, among other things, devices and methods that can be used to treat a patient, such as for locally treating target tissue including, but not limited to, endometriosis, menorrhagia, and intra-uterine growths such as polyps. As defined herein, "target tissue" refers to any biological tissue or a part thereof, including blood and/or vessels, which is the object of focused tissue ablation and includes, e.g., a group of cells, a tissue, a body part or an organ.

The device can include an outer shaft that can be inserted into the patient. A surgical instrument having a treatment end can be translatable within the outer shaft to extend from the outer shaft and deliver the PDT therapy to the patient. The treatment end can include a light emitter and an applicator tip in a configuration such that the photosensitizer and illumination provided by the light emitter can be applied to the surface of a target tissue. As discussed more herein, the photosensitizer and illumination can be provided simultaneously, i.e., at the same time, during the procedure for providing PDT. In one example, the photosensitizer can initially be applied alone, but after a certain time limit, the illumination can be delivered with the continued application of the photosensitizer. In some examples, the photosensitizer can be applied to the surface of the target tissue and the illumination can be provided substantially simultaneously or subsequently. In this instance, the illumination can be provided subsequently after the application of the photosensitizer. For example, the illumination can be provided within 10 minutes of the application of the photosensitizer, such as about 9 minutes, 8 minutes, 7 minutes, 6 minutes, 5 minutes, 4 minutes, 3 minutes, 2 minutes, and 1 minute. In one example, the illumination occurs less than 1 minute such as within 40 seconds, 30 seconds, 20 seconds, 10 seconds, 5 seconds, and 3 seconds. Further, a combination of simultaneous application of the illumination and photosensitizer and staggered (or subsequent) application of illumination can be used during the procedure, as discussed more herein. Whether the photosensitizer and illumination are provided simultaneously, substantially simultaneously, or subsequently, can depend on a variety of factors such as the target tissue, the particular, photosensitizer, and desired treatment outcome.

FIG. 1 is a schematic illustration of therapy device 10 (also referred to herein as "device 10") that can apply PDT to target tissue. Therapy device 10 can comprise handle or handpiece 20, outer shaft 12, and surgical instrument 23. The surgical instrument 23 can deliver PDT by applying the photosensitizer and illumination to the target tissue such as a surface of the target tissue. The surgical instrument 23 can provide the photosensitizer via an applicator system 29 and can provide the illumination via a lighting system 21. The applicator system 29 can comprise an application shaft 28 and an applicator tip 26. The lighting system 21 can comprise a light source 38, light delivery shaft 33, light conductor 32, and light emitter 24. The application tip 26 and the light emitter 24 can form a treatment end 22 of the surgical instrument 23 that deliver the PDT to the target tissue.

The outer shaft 12 can include an elongate member extending from a proximal portion 14 to a distal portion 16. The outer shaft 12 defines a lumen 19 extending from the proximal portion 14 to the distal portion 16 including a distal opening 18. The handpiece 20 can be mounted or connected to the proximal portion 14 of the outer shaft 12. Portions of the applicator system 29 and the lighting system 21 can run within or along the outer shaft 12, such as from the proximal portion 14 to the distal portion 16.

In examples, the outer shaft 16 can be sized, shaped, or arranged for performing laparoscopic procedures in conjunction with a laparoscope as well as performing transcervical procedures. As such, shaft 16 can be inserted into an incision in the epidermis of a patient, through a body cavity of the patient and into an organ or transcervically into a uterus. Thus, it is desirable for the diameter or cross-sectional shape of shaft 16 to be as small as possible to facilitate minimally invasive surgical procedures and minimal dilation of the cervix. The outer shaft 12 can be rigid and formed from a metal or plastic material. In an example, the outer shaft 12 can have a diameter of less than about 6 mm. The proximal portion 14 can be near an operator when the device 10 is in use.

A drug-delivery conduit 30 can be defined by the application shaft 28. A drug source 46 can be connected to the drug-delivery conduit 30 at the proximal end 14 to deliver the photosensitizer to the applicator tip 26. The applicator tip 26 is configured to apply the photosensitizer to the target tissue in a manner specific to the type of treatment and anatomy being treated. The therapy device 10 can further comprise a power source or generator 48 that can be coupled to the drug source 46 via linkage 50 and to the therapy device 10 via linkage 44. The drug source 46 can be removable (or refillable), thereby allowing for attachment or use of different photosensitizers during a treatment.

Handpiece 20 can comprise any device suitable for facilitating manipulation and operation of therapy device 10. Handpiece 20 can be located at the proximal portion 14 or another suitable location along shaft 12. In examples, handpiece 20 can comprise a pistol grip, a knob, a handlebar grip and the like. Actuation device 42 can be attached to handpiece 20 to operate linkages 44, 50. Actuation device 42 can comprise one or more of buttons, triggers, levers, knobs, dials and the like. Linkages 44, 50 can comprise any suitable device for allowing operation of therapy device 10 from handpiece 20. In examples, linkages 44, 50 can be a mechanical linkage, an electronic linkage, an electric linkage, a fluid linkage or an acoustic linkage.

Light conductor 32 can comprise a medium for transmitting light from light source 38 to light emitter 24. Light conductor 32 can be located within a light shaft 33 extending from the proximal portion 14 to the light emitter 24 at the distal portion 16. Light conductor 32 can comprise a material suitable for transmitting waves of electromagnetic radiation at various wavelengths. Light conductor 32 can be coupled to light source 38 via cable 36 and connector 34. Cable 36 can comprise an extension of light conductor 32 and can be fabricated from the same material as light conductor 32. In examples, light conductor 32 and cable 36 can comprise fiber optic cables. In examples, the fiber optic cables can comprise glass and plastic fibers jacketed with one or more protective coatings. Light emitter 24 can be located at or near the distal end of light conductor 32. Light emitter 24 can be coupled to light conductor 32 by any suitable means. In examples, light emitter 24 can comprise a lens for focusing or a diffuser for spreading light waves from light conductor 32. Light emitter 24 can be unidirectional or omnidirectional. Light emitter 24 can comprise a glass or plastic body of transparent material. However, in additional examples, a separate light emitter is not used and light conductor 32 can comprise an end-emitting fiber such that the distal or terminal end of light emitter 32 can comprise light emitter 32.

In an example, the light emitter 24 and the application tip 26 can be coupled such that they cannot move relative to each other. That is, they can be linearly locked together such that they move relative to the outer shaft 12 together. The light emitter 24 and application tip 26 can be located and the end of a single shaft or located at the end of two respective shafts (light shaft 33 and the applicator shaft 28), where the two shafts can be coupled together. In another example, the light emitter 23 and the application tip 26 are not linearly locked and can move relative to one another and to the outer shaft 12.

The light source 38 may be any suitable light source that emits a light beam with a wavelength that matches one of the absorption peaks of the photosensitizer drug. That is, the light source 38 should emit a photosensitizer activating light (referred to herein as "phototherapeutic light" or "therapy light") and is based on the type of photosensitizer drug used.

As mentioned, light source 38 can be coupled to light conductor 32 via cable 36. Connector 34 can comprise any suitable device for linking light conductor 32 and cable 36 such that fibers disposed therein can be adjoined in an end-to-end manner. As such, light source 38 can be located remotely from therapy device 10. In examples, light source 38 can comprise a stand-alone module couplable to the therapy device 10 via cable 36. In additional examples, light source 38 can be attached directly to the exterior of handpiece 20 via connector 34 without using cable 36. As such, light source 38 can be removable, thereby allowing for attachment of light generators that produce different intensities or wavelengths, which, as discussed below, can allow for activation of different types of photosensitizer drugs. In additional examples, light source 38 can be incorporated into handpiece 20 such that connector 34 is not used. In additional examples, light source 38 can be incorporated into generator 48 and cable 36 and cable 44 can be included in a common cable bundle. In additional examples, the light source 38 can be provided at the distal end of the light shaft 33 such that the light source 38 is coupled to a power source and the light is generated at the distal end of the light shaft 33 instead of generated and transmitted to the light emitter 24 using the light conductor 32.

The light from light source 38 can be transmitted through light shaft 33 using light conductor 32 to provide the photosensitizer activating light (illumination) with or without the aid of a separate light emitter device, such as light emitter 24. As mentioned, removable light generators can facilitate production of light at different wavelengths such that the activation wavelength can be matched for the particular photosensitizer drug used. This is beneficial as the particular photosensitizer drug used can depend on the type of target tissue, surrounding tissue/anatomy, and strength needed to treat the target tissue. As discussed herein, during a treatment of a target tissue, one or more photosensitizers can be applied to the target tissue to alter the intensity of the PDT. In an example, the drug source 46 and the light source 38 can be changed such that the wavelength of the light from the light source 38 matches the new photosensitizer so that different photosensitizers can be used. For example, depending on the target tissue and treatment intensity needed, different photosensitizers may be used during a single PDT treatment.

Actuation device 40 can be attached to handpiece 20 to operate linkage 36. Actuation device 40 can comprise one or more of buttons, trigger, lever, knobs, dials and the like. Linkage 36 can comprise any suitable device for allowing operation of one or more features of the lighting system 21 from handpiece 20. In examples, linkage 36 can be a mechanical linkage, an electronic linkage, an electric linkage, a fluid linkage or an acoustic linkage.

As discussed herein, the wavelength emitted from the light source 38 is matched with one of the absorption peaks of the selected photosensitizer. The estimated light intensity to be delivered depends on the lighting system 21, the mode of illumination used, the nature of the target tissue, and the objective of the treatment.

The drug source 46 can hold the photosensitizer of choice. As discussed herein, since the photosensitizer is being applied topically to the target tissue, a lower amount of the photosensitizer can be used and less is absorbed into the body as it is not injected intravenously or taken orally. Additionally, because the photosensitizer and illumination are provided substantially simultaneously and to the surface of the target tissue, there is no critical window in which a user needs to provide the illumination in order to provide effective and efficient PDT to a patient.

The photosensitizer can be selected from any suitable photosensitizer. An exemplary list of photosensitizers include, but is not limited to porphyrins, 5-Aminolaevulinic acid (ALA), chlorin, pyrrole-derived macrocyclic compounds, porphyrins, chlorins, bacteriochlorins, isobacteriochlorins, phthalocyanines, naphthalocyanines, porphycenes, porphycyanines, pentaphyrin, sapphyrins, texaphyrins, phenoxazine dies, phenothiazines, chaloorganapyrylium dyes, triarylmethanes, rhodamines, fluorescenes, azapophyrins, benzochlorins, purpurins, chlorophylls, verdines, and derivatives thereof.

The manner in which the photosensitizer is applied to the target tissue via the applicator tip 26 can depend on the location and type of target tissue. For example, the photosensitizer can be applied in a stream in a high or low pressure low, as a spray, as an atomized spray (a mist or fog), or as a paste.

As discussed herein, the photosensitization of the drug elicits the transfer of energy and can ablate the target tissue. Ablation can include, for example, removal or destruction of the target tissue by the application of PDT. In some cases, ablation can cause tissue necrosis. In on example, the target tissue can scar in response to ablation, preventing it from copious bleeding and producing menorrhagia effects.

Further, while not shown in FIG. 1, a gas-conduit can be provided in the therapy device 10 to provide an oxygen stream to the target tissue. The oxygen concentration at the target tissue can change the results from the PDT. For example, low oxygen content can reduce phototoxicity preventing the PDT from achieving its full therapeutic potential. Thus, any of the therapy devices disclosed herein can be configured to supply oxygen to the target tissue to increase the oxygen at the target tissue and maximize the therapeutic potential of the PDT.

Figure 2:
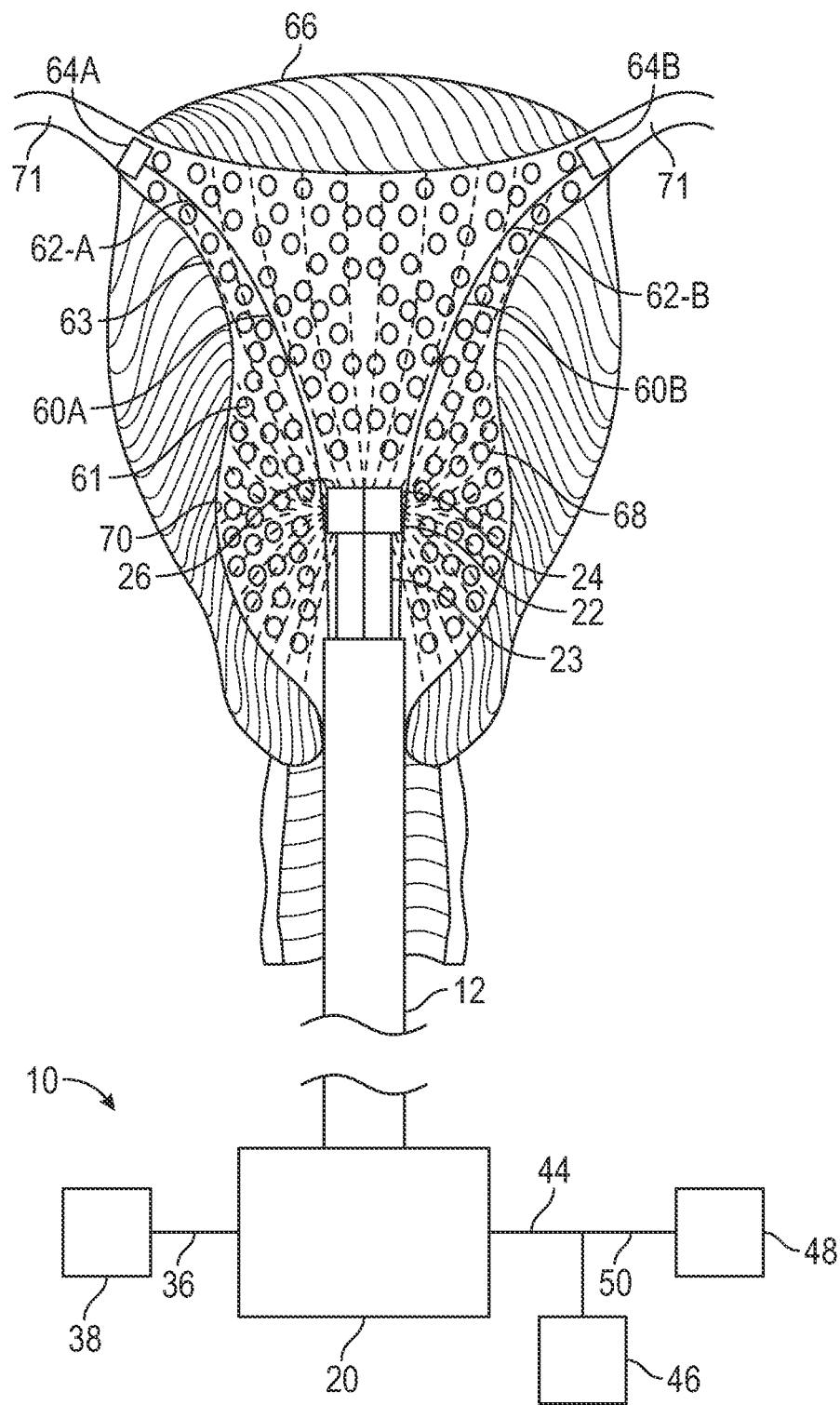
FIG. 2 is a schematic illustration of a therapy device providing PDT to a patient having menorrhagia, according to one example of the present disclosure.

FIG. 2 is a schematic illustration of a therapy device 10 providing PDT to a patient having menorrhagia, according to one example of the present disclosure. The outer shaft 12 has been inserted into a body cavity (the uterus 66) and the surgical instrument 23 is advanced from the outer shaft 12 such that the treatment end 22 is at a desired position. In this example, since the therapy device 10 is treating for menorrhagia, the photosensitizer 61 can be applied in a mist form from the applicator tip 26 such as to most efficiently come into contact with the surface of the uterine wall 70. However, any application method of the photosensitizer is contemplated.

Phototherapeutic light 63 (the photosensitizer activating light) is delivered to illuminate the intrauterine wall 70. The phototherapeutic light 63 can be administered at the same time, or substantially the same time, as the photosensitizer 61. The therapy device 10 allows the selective destruction of the intrauterine wall 70 because the light is delivered during the time of maximum photosensitizer concentration at the surface of the target tissue. That is, the light is delivered as the photosensitizer is continuously being applied to the surface of the target tissue. The dose, amount, and type of the photosensitizer, as well as the length of the illumination, can depend on the particular patient and desired tissue outcome. Thus, in one example, the protocol for PDT can include applying the photosensitizer/illumination at the same time for a time period.

As discussed herein, the type of abnormality being treated can determine the protocol used during the PDT. For example, in other examples, the protocol can include switching between applying the PDT (photosensitizer/illumination) and not applying the PDT. For example, a duty cycle of applying the PDT can be applied when treating the patient. The type of photosensitizer can also determine the type of protocol used. In an example, some photosensitizers can work immediately, and their therapeutic affect is done whereas other photosensitizers can have a longer effective duration. Thus, an operator can apply PDT such as applying the photosensitizer/illumination and then diagnosis the target tissue after a time period to determine if additional sessions of PDT is necessary.

In one example a coaxial optical fiber can be used and includes a visual light that can connect to a camera and a treatment light to apply the wavelength that matches the photosensitizer being used. The operator can then switch between applying PDT and diagnosing until the target tissue is sufficiently treated. In one example, the diagnosing can occur while the PDT is being applied. However, in other examples, the diagnosing can occur after the PDT (photosensitizer/illumination) has stopped and the effective duration of the photosensitizer is over. An optical system and/or imaging system can be used to identify target tissues, immediately measure the treatment of the target tissue to determine if more treatment is needed, and determine if the procedure is complete. One example of such an optical system is disclosed in U.S. Provisional Patent Application 62/940,328, filed Nov. 26, 2019, titled "Surgical devices with Integrated Lighting Systems," which is incorporated by reference in its entirety.

In another example, the same effect can be realized by applying the photosensitizer 61, stopping the application of the photosensitizer 61, and illuminating the target tissue within a certain time limit after the application of the photosensitizer 61 has stopped. This sequence can be repeated numerous times until the desired tissue outcome is realized. Thus, in one example, the protocol for delivering the PDT can be: apply photosensitizer-illuminate-apply photosensitizer-illuminate-apply photosensitizer-illuminate, etc. The time limit can vary and be less than 5 minutes, such as but not limited to less than 1 minutes, and less than 10 seconds.

Optionally, the therapy device 10 can include fallopian blockers 60A, 60B that can extend from the outer shaft 12. The fallopian blockers 60A, 60B include elongate member 62A, 62B with block portions 64A, 64B that are configured to block the fallopian tubes 71 to minimize the photosensitizer 61 and phototherapeutic light 63 from entering the fallopian tubes 71 and ablating unintended target tissue.

As shown in FIG. 2, the therapy device 10 is applying a global application of PDT for treating menorrhagia where the fallopian tubes are tissue that is meant to not receive treatment. However, there may be other instances where a large area of tissue is the target tissue but there may be areas that are not mean to receive treatment other than the fallopian tubes. Optionally, a pretreatment can be performed on the area around the target tissue that is not meant to receive the treatment. The pretreatment can include applying a blocking coating to tissue that is not meant to receive the PDT. The blocking coating can prevent the photosensitizer from contacting/absorbing into the tissue and/or block the wavelengths from the light source 38. In an example, the therapy device 10 or a separate device can be used to apply the blocking coating to a surface of tissue not meant to receive the PDT treatment. Examples of the blocker coating can include, but are not limited to, hydrophobic coatings, beeswax, and mucosal adhesive, among others, that have the properties to prevent attachment/contact of the photosensitizer to the tissue or to block the wavelength generated from the light source 38.

As discussed herein, the light emitter 24 and application tip 26 can be linearly locked together. In an example, during the treatment of the intrauterine wall 70, while the PDT is being delivered, the light emitter 24 and the application tip 26 can be moved along a longitudinal axis (together) within the uterus 66 to treat the target tissue. Alternatively, the light emitter 24 and the application tip 26 can move independently of each other such that one may remain in a stationary position while the other one moves linearly. Moreover, they both can move at the same time in different directions or at different speeds relative to one another. In one example, the applicator tip 26 position is maintained constant while applying the photosensitizer 61 and the light emitter 24 is moved back and forth along a longitudinal axis to effectively apply and thoroughly illuminate the intrauterine wall 70. Further, the surgical device 23 can be rotated about a longitudinal axis to increase the efficiency of the PDT.

Figure 3:
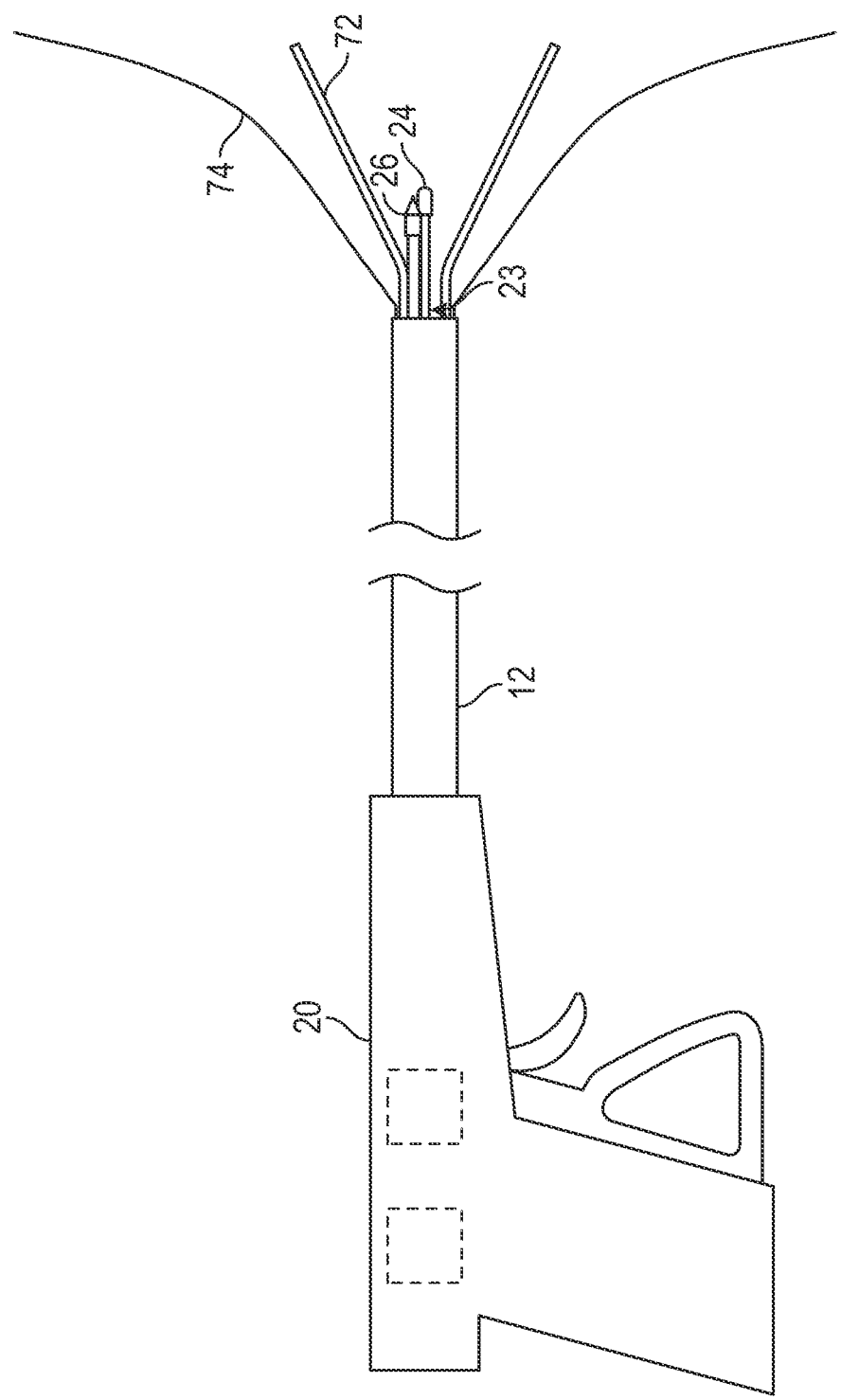
FIG. 3 is a schematic illustration of a therapy device that can provide PDT including a phototherapeutic light containment device and a distension member, according to one example of the present disclosure.
Figure 4:
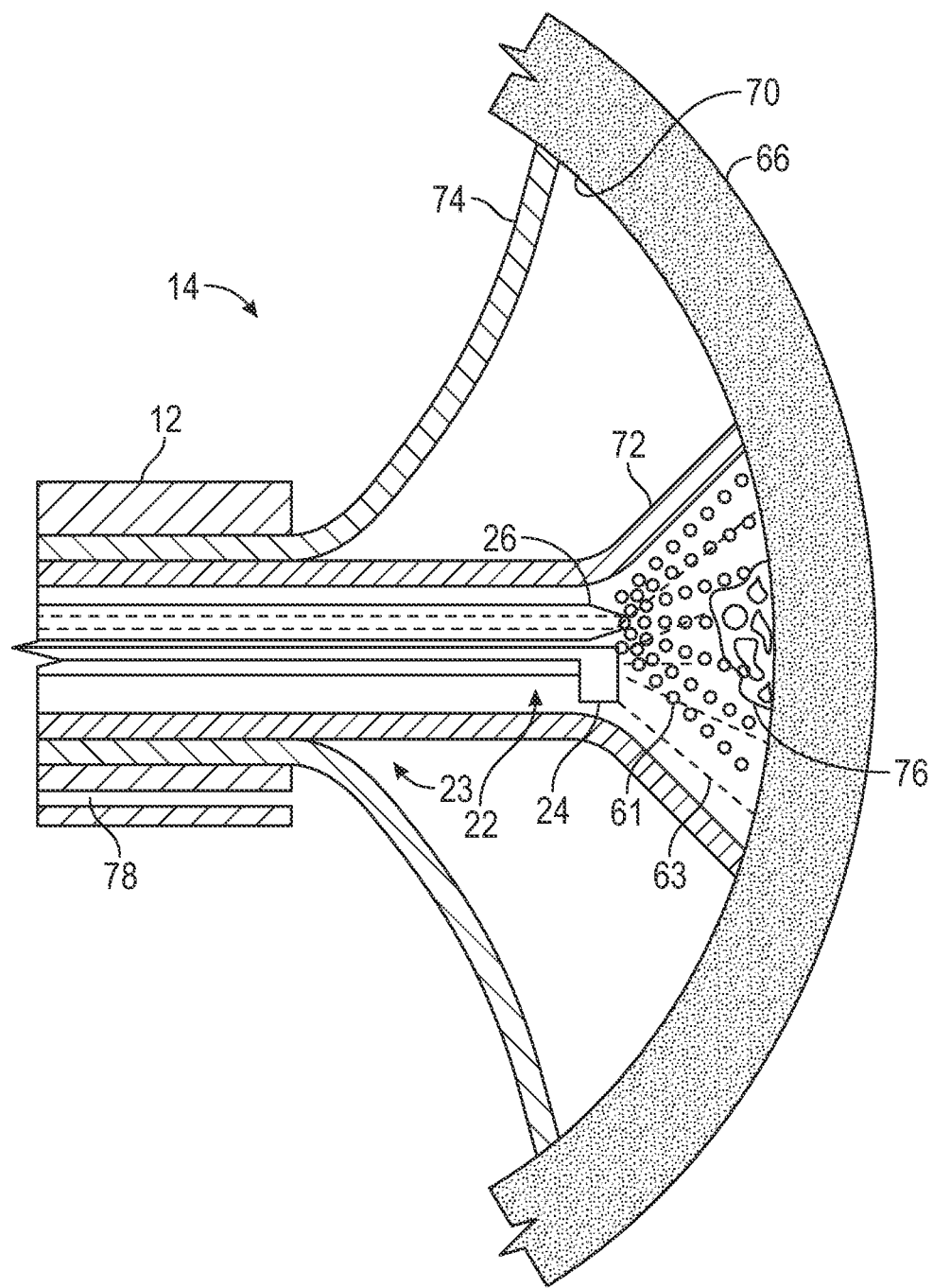
FIG. 4 is a close-up view of the distal portion of the therapy device shown in FIG. 3 applying PDT to a patient having an intra-uterine polyp.

FIG. 3 is a schematic illustration of the therapy device 10 including a distension member 74 and a phototherapeutic light containment device 72. FIG. 4 is a close-up view of the distal portion of the therapy device shown in FIG. 3 applying PDT to a patient having an intra-uterine polyp. The distension member 74 and a phototherapeutic light containment device 72 are optional and can be utilized to increase the efficiency of the application of PDT in certain instances. FIGS. 3 and 4 will be discussed together.

The distention member 74 can be translatable within the outer shaft 12 and configured to distend a patient's uterus. Distension member 74 could also be utilized in the example illustrated in FIG. 2 for treating menorrhagia. The distention member 72 can have a non-expanded position and an expanded position. For example, while positioned within the outer shaft 12, the distension member 72 can be in the non-expanded positioned (compressed state) and as the distension member 72 advances from the outer shaft 12, the distension member 72 transitions from the non-expanded positioned to the expanded position (uncompressed state) to distend a body cavity such as a uterus. While any distension structures are contemplated, in one example, the distension member 72 includes two or more elongated legs. The distension member 72 can be formed from, but not limited to, silicone, PET, polyurethane, rubber, or the like.

Figure 6:
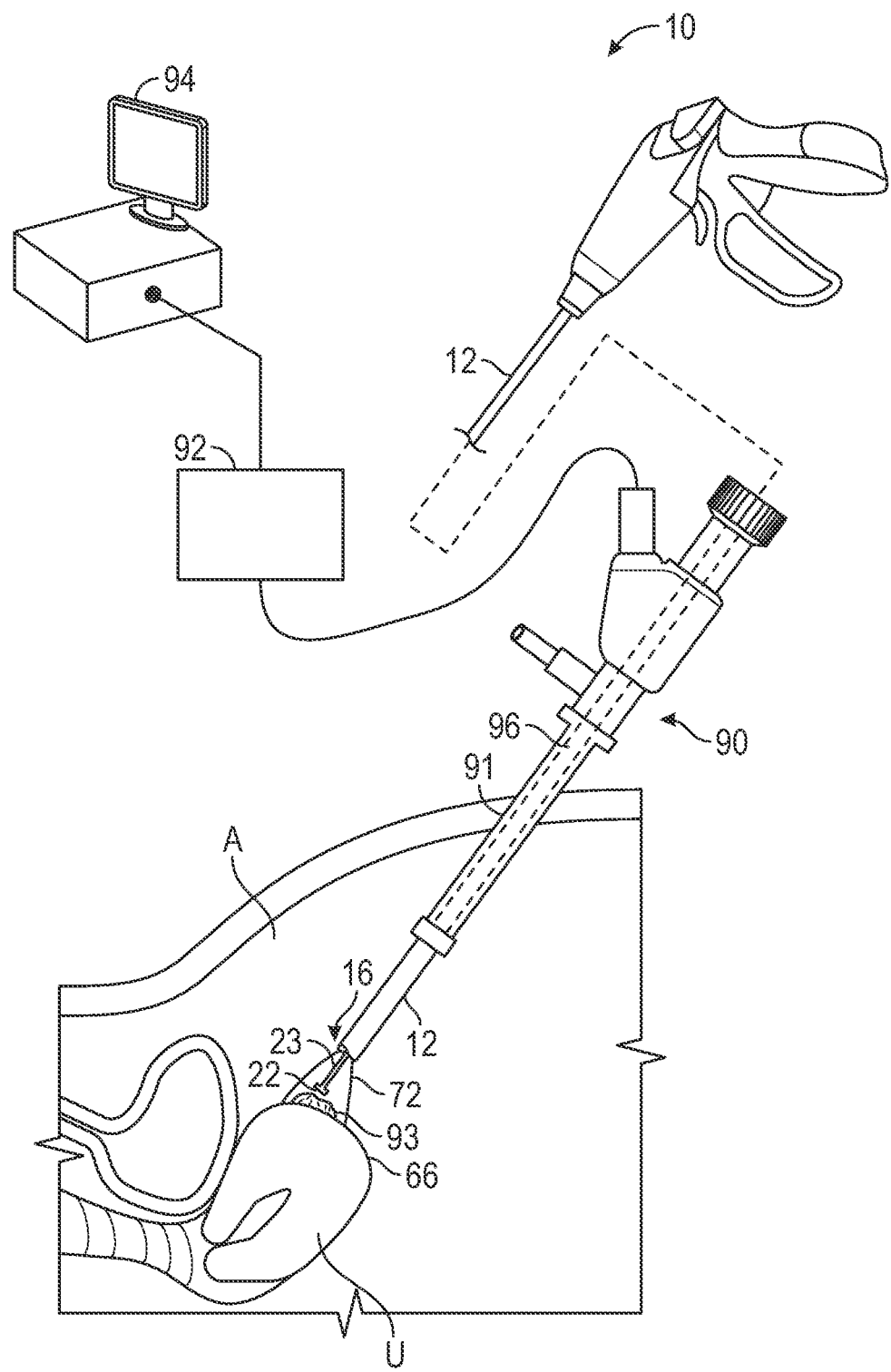
FIG. 6 is a schematic diagram illustrating a laparoscopic surgical procedure to provide PDT to a patient having endometriosis, according to an example of the present disclosure.

That phototherapeutic light containment device 72 can be used to contain the illumination to a particular area. For targeted PDT such as applying PDT to a polyp (as shown in FIG. 4) or endometriosis (as shown in FIG. 6), it may be easier to contain the light than it would be to contain the application of the photosensitizer to a particular location. In certain instances, the photosensitizer characteristics such as viscosity can be changed to allow the photosensitizer to stay in a particular location for an extended period of time. For example, the photosensitizer can be applied in a liquid, gel, or paste form depending on the location and features of the therapy device 10.

Similar to the distension member 74, the phototherapeutic light containment device 72 can have a non-expanded position and an expanded position. For example, while positioned within the outer shaft 12, the phototherapeutic light containment device 72 can be in the non-expanded positioned (compressed state) and as the phototherapeutic light containment device 72 advances from the outer shaft 12, the phototherapeutic light containment device 72 transitions from the non-expanded positioned to the expanded position (uncompressed state) and can be advanced such that a distal end of the phototherapeutic light containment device 72 contacts an area around the target tissue 76 (uterine polyp). The phototherapeutic light containment device 72 surrounds the treatment end 22 of the surgical instrument 23 to contain the phototherapeutic light 63 to a desired location while the photosensitizer 61 is being delivered. In order to contain the phototherapeutic light 63, the phototherapeutic light containment device 72 is formed from a material that does not transmit the phototherapeutic light.

Therapy device 10 can also include a gas-conduit 78 located, e.g., in the wall of the outer shaft 12 to deliver a gas. The gas can assist in distending the body cavity but can also be used for increasing the reactivity of the photosensitizer when the gas is oxygen. While shown in the wall of the outer shaft 12, the oxygen gas flow can be supplied in a variety of ways. In one example, a flow of oxygen can be supplied through the phototherapeutic light containment device 72. However, other configurations are contemplated.

Figure 5A:
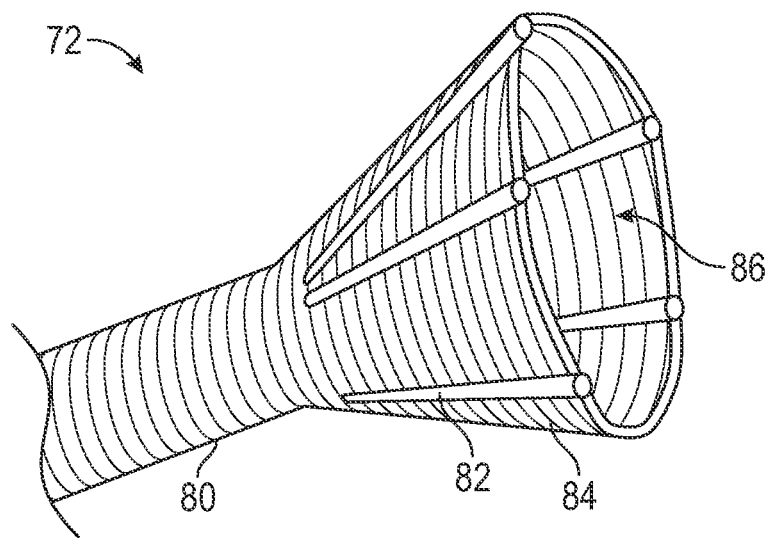
FIG. 5A is a schematic perspective view of a phototherapeutic light containment device, according to one example of the present disclosure.
Figure 5B:
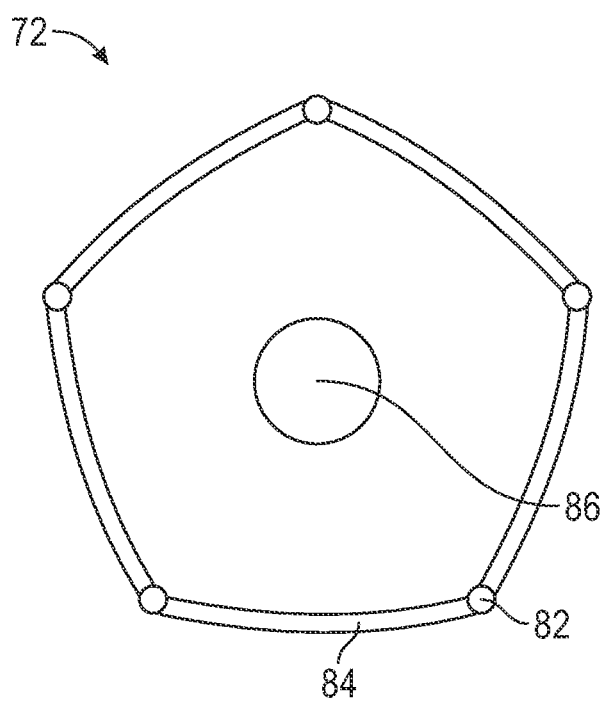
FIG. 5B is a schematic end-view of the phototherapeutic light containment device shown in FIG. 5A.

FIG. 5A is a schematic perspective view of the phototherapeutic light containment device 72 and FIG. 5B is a schematic end-view of the phototherapeutic light containment device 72. FIG. 5A illustrates the phototherapeutic light containment device 72 in an expanded state. The phototherapeutic light containment device 72 can include an elongate body 80 and a plurality of flexible members 82 connected by a flexible material 84. The area defined by the distal end of the phototherapeutic light containment device 72 can vary and be dependent on how far the phototherapeutic light containment device 72 is extended out of the outer shaft 12. The phototherapeutic light containment device 72 can define a lumen 86 that can receive the surgical instrument 23 and or provide an oxygen gas flow.

Figure 9:
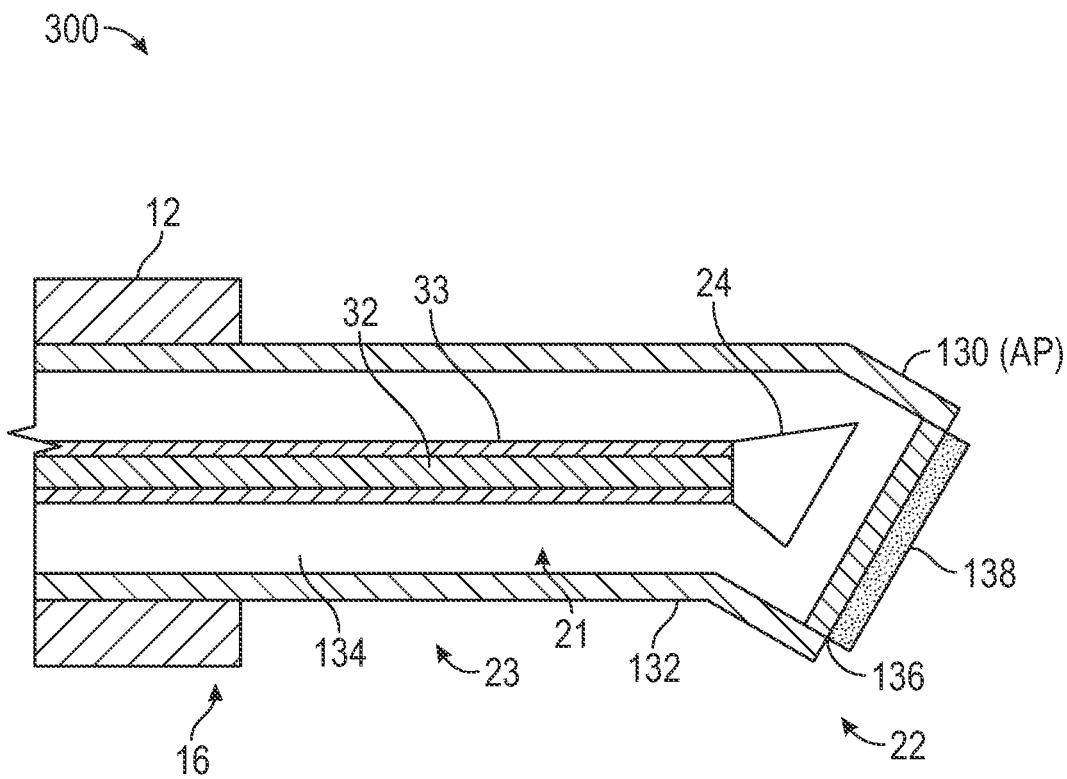
FIG. 9 is a schematic cross-sectional view of another example of a therapy device that can provide PDT to a target tissue, according to one example of the present disclosure.

FIG. 6 is a schematic diagram illustrating a laparoscopic surgical procedure to provide PDT to a patient having endometriosis. The surgical procedure can comprise an open procedure or a laparoscopic procedure. FIG. 6 illustrates a laparoscopic procedure being performed with the therapy device 10 shown in FIG. 4 without the distention member 74. The surgical procedure can be performed to remove or otherwise ablate target tissue that is diseased or invasive. FIG. 6 illustrates a surgical procedure being performed to remove endometrium tissue from the cavity of abdomen A that has grown outside of uterus U. FIG. 9 illustrates an operating room environment where laparoscope 90 is coupled to camera 92 and display 94.

The therapy device 10 can be inserted into passage 96 of the laparoscope 90. As shown, the distal portion 16 of the outer shaft 12 protrudes from passage 96 and is located inside the abdomen A. The treatment end 22 of the surgical instrument 23 can be advanced from the outer shaft 12 and positioned to deliver the PDT. As seen in FIG. 6, the phototherapeutic light containment device 72 is deployed and surrounds the treatment end 22 as well as confines the phototherapeutic light to the target tissue 90 (endometriosis).

Figure 7:
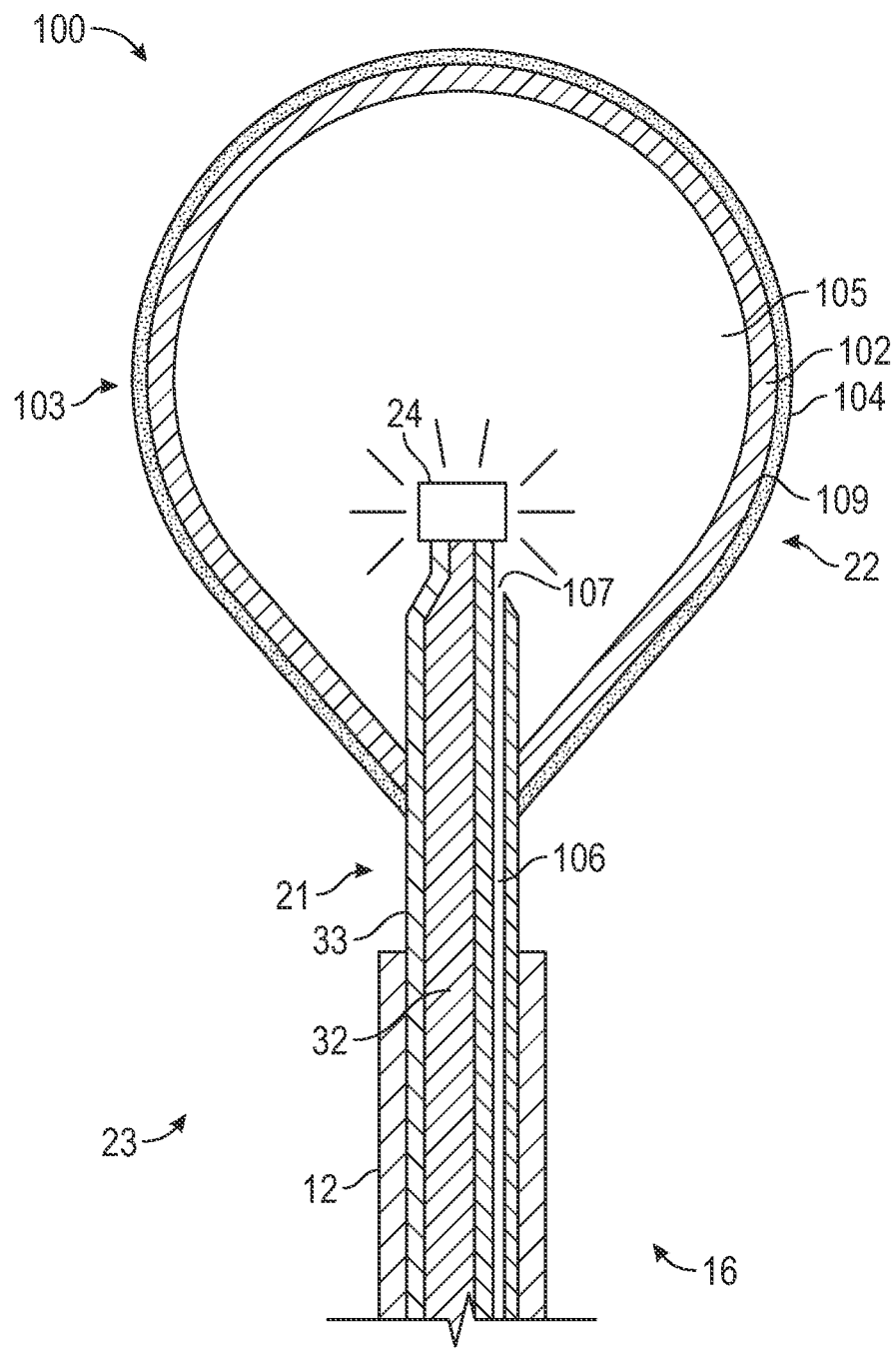
FIG. 7 is a schematic cross-sectional view of another example of a therapy device that can provide PDT to a target tissue, according to one example of the present disclosure.
Figure 8:
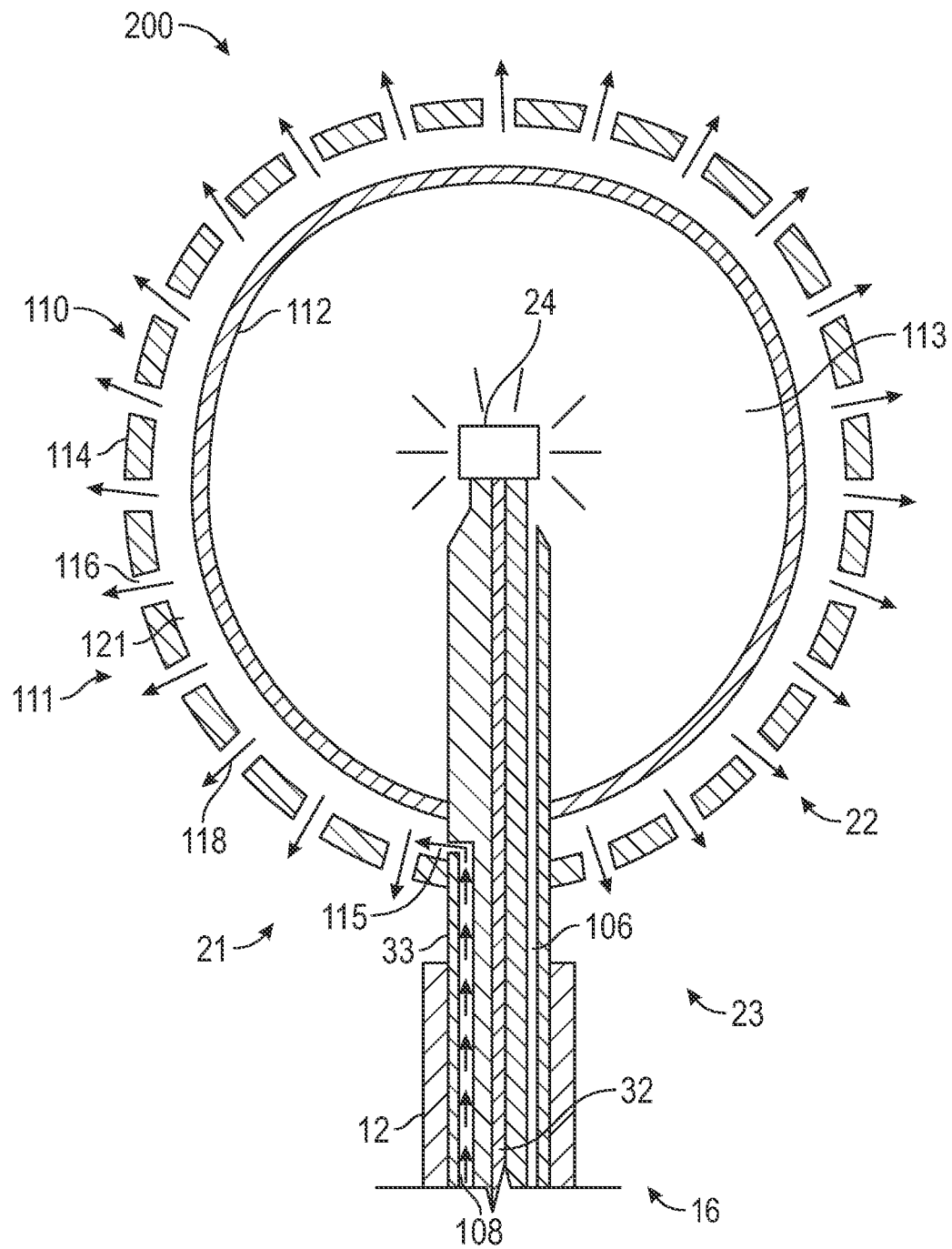
FIG. 8 is a schematic cross-sectional view of another example of a therapy device that can provide PDT to a target tissue, according to one example of the present disclosure.

FIGS. 7 and 8 illustrate portions of other examples of therapy devices 100, 200 such as for one or more intrauterine tissue effects. FIG. 7 illustrates therapy device 100 including a treatment end 22. The treatment end 22 includes the lighting system 21 as disclosed herein and an applicator system 103. The applicator system 103 includes an expandable medium 102 including a layer 104 of the photosensitizer on the outer surface 109 of the expandable medium 102. The expansion of the expandable medium 120 is configured to apply the photosensitizer to the target tissue. The lighting system 21 can include the light emitter 24, the light shaft 33, and the light conductor 32. However, light shaft 33 as shown in FIG. 7 can includes a medium-delivery conduit 106 in fluid communication with an interior 105 of the expandable medium 102. The medium-delivery conduit 130 can run within or along the light shaft 33. A medium source such as gas or liquid can be connected to the medium-delivery conduit 106 at the proximal end of the light shaft 12. The expandable medium 102 can be, for example, elastic and inflatable, such as using a balloon-type material and is transparent to the wavelength generated by the light source.

The applicator system 103 includes a layer 104 of the photosensitizer on an outer surface 109 of the expandable medium 103. In one example, the layer 104 can be a composite material that includes the photosensitizer.

The expandable medium 102 can have both a lower profile state and a relatively higher profile state. In the lower profile state, the expandable medium 102 can be, for example, collapsed on light shaft 33. In the lower profile state, the expandable medium 102 can be, for example, narrower in profile, such as for easier insertion into a patient. In the lower profile state, the expandable medium 102 can have a lateral profile outer dimension, such as a diameter, of less than about 6 mm, such as for easier transcervical insertion into the patient.

In the higher profile state, the expandable medium 102 can be expanded to a larger size, such as a larger diameter, cross-section, or volume, such as while within the uterus. When in the relatively higher profile state, the expandable medium 102 can have a lateral profile outer dimension, such as a diameter, of about 3 cm to about 4 cm.

The expandable medium 102 can include, for example, a urethane material. In some cases, the expandable medium 102 can include more than one layer of material, such as discussed below with reference to FIG. 8.

The medium-delivery conduit 106 can deliver a medium to the expandable medium 102 at or via an outlet 107. When deployed, the expandable medium 102 can cover or encase the outlet 107 so that the fluid can be delivered directly into the expandable medium 102. The fluid can include, for example, water, saline, oxygen, carbon dioxide or other suitable liquid or gas.

In some cases, the outlet 107 can include a valve in fluid communication with the medium-delivery conduit 106. The valve can be configured to be user-triggered to allow or prevent or otherwise control delivery of the medium towards expandable medium 102 via the valve. The operator can trigger the valve, for example, by a button or trigger on the hand piece. In some cases, the operator can trigger the valve by a foot pedal or other actuator coupled to the device 100.

The medium can be provided to the expandable medium 102 via the fluid-delivery conduit 106 from a medium source. In an example, the medium source can include a pre-filled syringe such as can be integrated with or attached to the hand piece. The syringe can have, for example, a plunger, such as can be actuated by a coiled spring, or can be manually actuated by the operator. The fluid source can include a tube, hose, pump, or combination thereof, such as for connecting the device to a larger canister, container, faucet, or other reservoir holding the fluid.

In some cases, the operator can use the device 100, for example, by inserting the distal portion 16 with the expandable medium 102 in a lower profile state (e.g., compacted) into the uterus of the patient, through the cervix. The operator can determine the correct placement of the device 100 in the patient, in some cases, by visual confirmation, through a scope (such as an endoscope) or camera integrated into the device. In some cases, the operator can use other imaging technology such as ultrasound. In other examples, where the operator intends to have the expandable medium 103 touch, extend, or distend the uterine wall, the operator can physically detect when the device 100 touches the uterine wall. The applicator system 103 includes a layer 104 of the photosensitizer on an outer surface 109 of the expandable medium 103.

After insertion, the operator can actuate the medium source so that the medium can be delivered down the medium-delivery conduit 106 and dripped, sprayed, or poured into the expandable medium 102, causing the expandable medium 102 to swell with the medium from a lower profile state (e.g., compacted) to a higher profile state (e.g., expanded), and partially or wholly filled with fluid. At the higher profile state, the layer 104 of the photosensitizer can contact the interior wall of the uterus. Subsequently or simultaneously, the user can activate the light so that the light emitter 24 can emit phototherapeutic light to illuminate the uterus and cause the activation of the photosensitizer.

The produced energy can ablate the endometrium. Ablation can include, for example, removal or destruction of the target tissue. In some cases, ablation can cause tissue necrosis. The target tissue can scar in response to ablation, preventing it from copious bleeding and producing menorrhagia effects.

FIG. 8 illustrates therapy device 200 for providing PDT. The device 200 can include the outer shaft 12, a surgical device 23 including the lighting system 21, and an applicator system 111. The applicator system 111 includes an expandable medium 110 including a first layer 112 and a second layer 114. As discussed herein, the expansion of the expandable medium 110 is to distend the uterus as well as apply the photosensitizer to the surface of the target tissue. The lighting system 21 can have the light emitter 24, the light shaft 33, and the light conductor 32. However, light shaft 33 as shown in FIG. 8 includes a medium-delivery conduit 106 in fluid communication with an interior 113 of the expandable medium 110. The medium-delivery conduit 106 can transition the expandable medium 110 from the low-profile state to the higher profile state as described in FIG. 7.

In the device 200, the expandable medium 110 can include a second layer 114 for delivering the photosensitizer. The device 200 includes a drug-delivery conduit 108 located, e.g., within the light shaft 33. The drug-delivery conduit 108 can run along the length of the light shaft 33 to an outlet 115. In an example, the outlet 115 is fully encompassed by the first layer 112 and the second layer 114.

The second layer 114 is porous and includes pores 116 that are in fluid communication with the drug-deliver conduit 108. The second layer 114 can be made of a material that interacts well with the target tissue, without causing damage to the target tissue. In some cases, when the expandable medium 110 is in a higher profile state, the second layer 114 can touch or directly interact with the target tissue. In some cases, where the second layer 114 touches the target tissue, the expandable medium can extend or distend the uterine wall.

The medium-delivery conduit 106 can deliver the medium to the expandable medium 110. For example, the medium can be provided to the interior 114 of the first layer 112 of the expandable medium 110 to transition the expandable medium 110 to the higher profile state. Once in the higher profile state, the drug-delivery conduit 108 can deliver the photosensitizer to the expandable medium 110 at or via an outlet 115. The photosensitizer can flow from the drug-delivery conduit 108, into a space 121 between the first layer 112 and the second layer 114 of the expandable medium 110, and out the pores 116 of the second layer 114 and contact the inner wall of the uterus.

In some cases, the outlet 115 can include a valve in fluid communication with the drug-delivery conduit 108. The valve can be configured to be user-triggered to allow or prevent or otherwise control delivery of the photosensitizer towards the expandable medium 110 via the valve. The operator can trigger the valve, for example, by a button or trigger on the hand piece. In some cases, the operator can trigger the valve by a foot pedal or other actuator coupled to the device 100. The photosensitizer can be provided to the expandable medium 110 via the drug-delivery conduit 108 from a photosensitizer source.

In some cases, the operator can use the device 200, for example, by inserting the distal portion 16 with the expandable medium 110 in a lower profile state (e.g., compacted) into the uterus of the patient, through the cervix. The operator can determine the correct placement of the device 100 in the patient, in some cases, by visual confirmation, through a scope (such as an endoscope) or camera integrated into the device. In some cases, the operator can use other imaging technology such as ultrasound. In other examples, where the operator intends to have the expandable medium 110 touch, extend, or distend the uterine wall, the operator can physically detect when the device 200 touches the uterine wall. The applicator system 111 includes the expandable medium 110 including the first layer 112 and the second layer 114 (porous layer).

After insertion, the operator can actuate the medium source so that the medium can be delivered down the medium-delivery conduit 106 and dripped, sprayed, or poured into the expandable medium 110, causing the expandable medium 110 to swell with the medium from a lower profile state (e.g., compacted) to a higher profile state (e.g., expanded), and partially or wholly filled with fluid. At the higher profile state, the second layer 114 can contact the interior wall of the uterus. Once in the higher profile state, the operator can actuate the photosensitizer source so that the photosensitizer can be delivered down the drug-delivery conduit 108 and dripped, sprayed, or poured into the space 121 between the first layer 112 and the second layer 114 such that the photosensitizer flows through the pores 116 and contacts the target tissue. Subsequently or simultaneously, the user can activate the light so that the light emitter 24 can emit phototherapeutic light to illuminate the uterus and cause the activation of the photosensitizer. While shown with one drug-delivery conduit 108, one or more drug-delivery conduits can be utilized.

The embodiment shown in FIG. 8 includes a two-layer balloon configuration. However, the second porous layer could also be a sponge that can receive the photosensitizer from the drug-delivery conduit 108 and deliver the photosensitizer to the target tissue.

The produced energy can ablate the endometrium. Ablation can include, for example, removal or destruction of the target tissue. In some cases, ablation can cause tissue necrosis. The target tissue can scar in response to ablation, preventing it from copious bleeding and producing menorrhagia effects.

FIG. 9 illustrates therapy device 300 for providing targeted PDT. The device 300 can include the outer shaft 12, a surgical device 23 including the lighting system 21, and an applicator system 130. The lighting system 21 can have the light emitter 24, the light shaft 33, and the light conductor 32. The applicator system 130 includes an applicator shaft 132 defining a lumen 134 that can receive a portion of the lighting system 21. For example, the light emitter 24, the light shaft 33, and the light conductor 32 can extend within the lumen 124. The applicator shaft 132 includes a cover 136 such as a lens located at the distal end. The cover 136 is a phototherapeutic light transparent lens such that the phototherapeutic light generated from a light source can transmit through the cover 136. The cover 136 includes a layer 138 of the photosensitizer.

In some cases, the operator can use the device 300, for example, by inserting the distal portion 16 into the patient, through the cervix or through an incision during a laparoscopic procedure. The operator can determine the location of the target tissue by visual confirmation, through a scope (such as an endoscope) or camera integrated into the device. In some cases, the operator can use other imaging technology such as ultrasound. The operator can guide the surgical instrument 23 such that the layer 138 of photosensitizer material contacts a surface of the target tissue. Simultaneously, or shortly thereafter contact is made with the target tissue, the operator can activate the light source such that the phototherapeutic light generated can be delivered to the target tissue via the light emitter 24.

The produced energy can ablate the target tissue. Ablation can include, for example, removal or destruction of the target tissue. In some cases, ablation can cause tissue necrosis. The target tissue can scar in response to ablation, preventing it from copious bleeding and producing menorrhagia effects.

Figure 10:
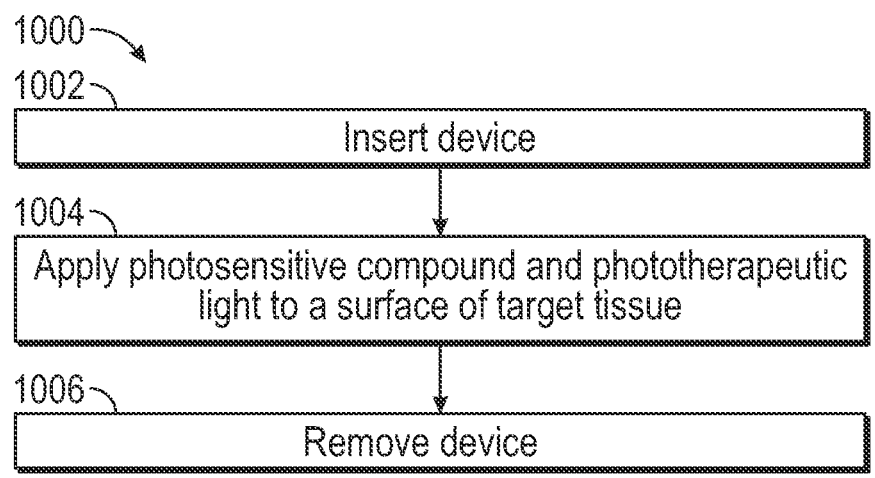
FIG. 10 is a schematic line diagram illustrating a method for providing PDT to a target tissue, according to one example of the present disclosure.

FIG. 10 is a line diagram illustrating method 1000 for performing a surgical procedure according the present disclosure. Method 100 can include providing PDT to a target tissue in a patient. The method 1000 can include inserting the device, at step 1002. That is, the distal portion 16 of the outer shaft 12 can be inserted into the patient. At step 1004, the method 100 can include applying a photosensitizer and phototherapeutic light to a surface of the target tissue. As discussed herein, the photosensitizer and the phototherapeutic light can be applied simultaneously, substantially simultaneously (within seconds/minutes), of a combination of both depending on the target tissue, treatment purpose, therapy device used, and type of photosensitizer. Additionally, the treatment can include applying one or more photosensitizers to the target tissue. Further, the protocol for the PDT therapy can include applying a duty cycle of the PDT. That is, the photosensitizer/illumination can be applied intermittently until the operator is satisfied with the tissue effects produced by the PDT. After applying the PDT treatment, the therapeutic device can be removed from the patient at step 1006.

Figure 11:
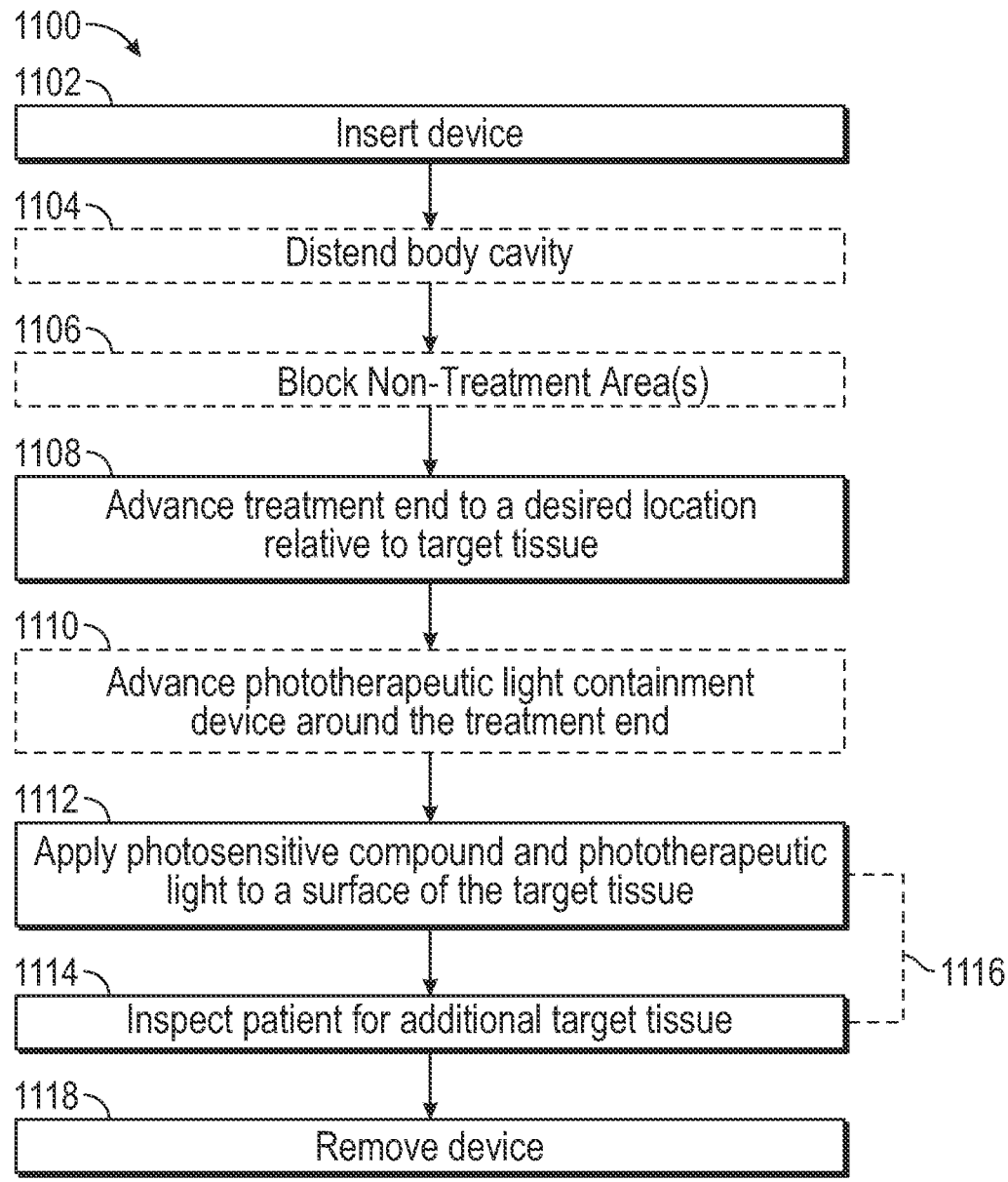
FIG. 11 is a schematic line diagram illustrating methods for providing PDT to a target tissue, according to one example of the present disclosure.

FIG. 11 is a line diagram illustrating a more detailed method 1100 for performing PDT according the present disclosure. Method 1100 can include providing PDT to a target tissue in a patient. The method 1100 can include inserting the device, at step 1102. That is, the distal portion 16 of the outer shaft 12 can be inserted into the patient. At optional step 1104, the method 1100 includes distending the body cavity. For example, as shown in FIG. 4, a distension member 74 can be deployed to distend the uterus. Distending the uterus may or may not be needed and can be determined by the operator.

At optional step 1104, the method 1100 can include blocking non-treatment area(s). In on example, step 1104 can include blocking the fallopian tubes. For example, as shown in FIG. 2, fallopian blockers 60A, B can be deployed from the outer shaft 12 to block the fallopian tubes 71 to prevent the photosensitizer and/or light from entering into the fallopian tubes, which may be considered non-target tissues in certain instances. In another example, a pretreatment can be done such as applying the blocking coating to non-treatment areas that will either prevent the photosensitizer from contacting and/or absorbing into the tissue and/or prevent the wavelengths from the light source from penetrating the blocking coating.

At step 1106, the treatment end is advanced to a desired location relative to the target tissue. At optional step 1110, the phototherapeutic light containment device can be advanced around the treatment end. For example, as shown in FIGS. 3 and 4, the phototherapeutic light containment device 72 can be deployed from the outer shaft 12 to contain the exposure of the generated phototherapeutic light to target the PDT to specific target tissue that may be adjacent to non-target tissue. At step 1112, the method 1100 can include applying a photosensitizer and phototherapeutic light to a surface of the target tissue, as discussed herein.

At step 1114, the method 1110 can include inspecting the patient for additional target tissue. That is, the operator can inspect the patient to determine if more PDT needs to be applied to a previously treated tissue or if there are additional areas of untreated target tissue that required PDT. If there is identified additional target tissue or there is part of a previously treated tissue that is in of additional treatment, at step 1116, the operator can go back to step 1112, and apply the PDT again until the user is satisfied that the target tissue is sufficiently treated or that all of the target tissue has been identified and sufficiently treated. At step 1118, the method 1100 includes removing the device from the patient.

Figure 12:
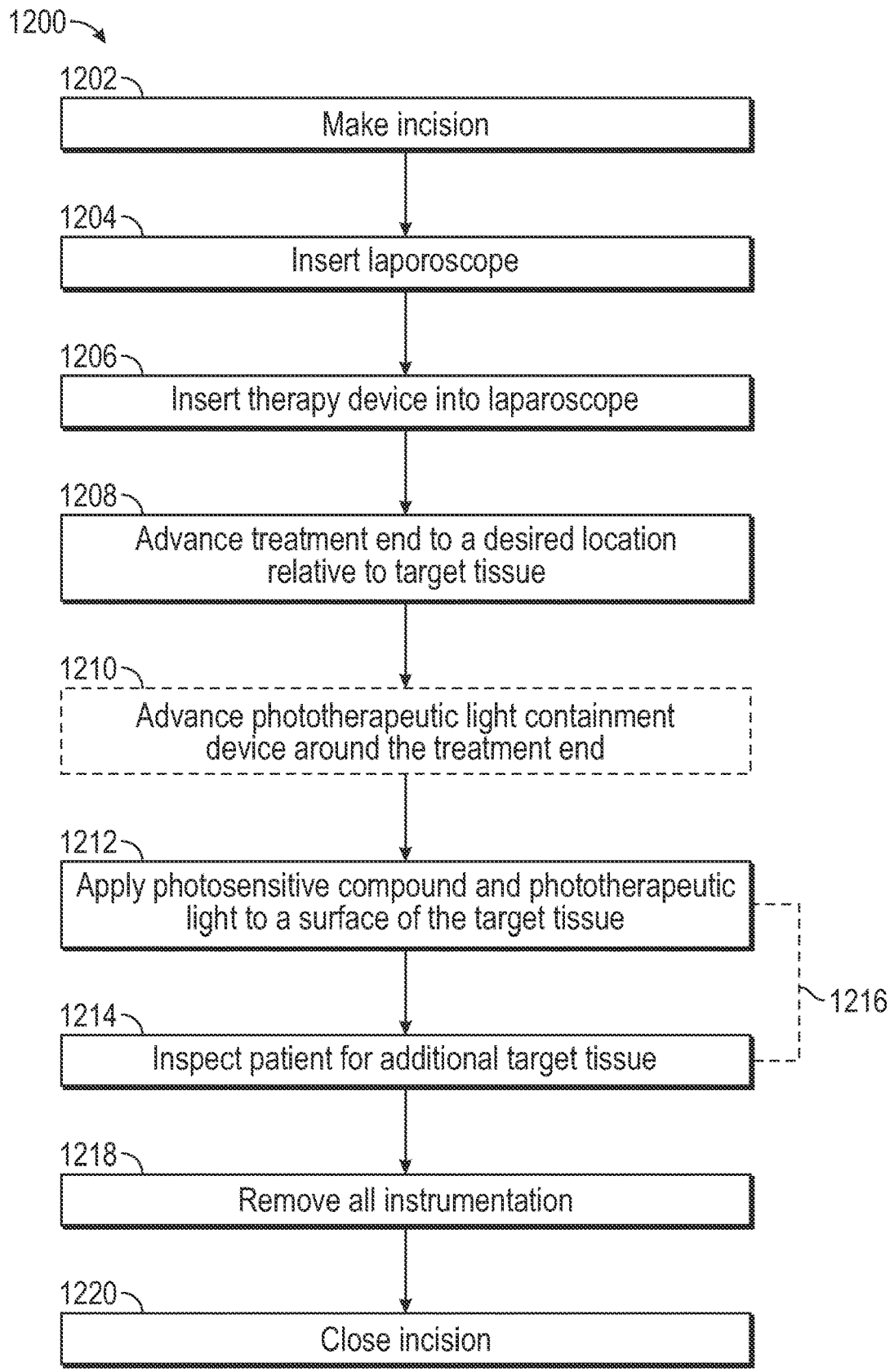
FIG. 12 is a schematic line diagram illustrating methods for providing PDT to a target tissue, according to one example of the present disclosure.

FIG. 12 is a schematic diagram of a laparoscopic surgical procedure being performed according to method 1200 of FIG. 6. Elements of FIG. 6 are not drawn to scale for illustrative purposes. FIGS. 6 and 12 are discussed concurrently.

The surgical procedure can comprise an open procedure or a laparoscopic procedure. FIG. 6 illustrates a laparoscopic procedure being performed therapy device 10 shown in FIGS. 3 and 4, but without the distension member 74. The surgical procedure can be performed to remove or otherwise abate target tissue that is diseased or invasive. FIG. 6 illustrates a surgical procedure being performed to remove endometrium tissue from the cavity of abdomen A that has grown outside of uterus U. However, the instruments and methods of the present application can be used to perform other procedures. The surgical procedure can be performed in an operating room in a hospital or out-patient facility. FIG. 6 illustrates an operating room environment where laparoscope 90 is coupled to camera 92 and display 94. The patient can be appropriately anesthetized.

At step 1202, incision 91 can be made in abdomen A of the patient. Incision 91 can be an incision having a sufficient length to form a portal for performing an open procedure. Incision 91 can also be a minimally invasive incision, such as one configured to receive laparoscope 90 as shown in FIG. 6.

At step 1204, laparoscope 90 can be inserted into incision 91. Laparoscope 90 can be coupled to camera 92 for viewing tissue within abdomen A of the patient internal to incision 91. Laparoscope 90 can include passage 96 that extends through incision 91 to allow access to internal tissue of the patient from outside the patient.

At step 1206, a therapy device, such as therapy device 10 having surgical instrument 23 of FIG. 4, can be inserted into incision 91. For example, the surgical instrument 23 can be inserted into passage 96 of laparoscope 90. Specifically, shaft 12 of therapy device 10 can be inserted through passage 96 such that the distal end 16 protrudes from passage 67 and is located inside abdomen A. At step 1208, the treatment end 22 including the light emitter 24 and the applicator 26 can be advanced from the outer shaft 12 and be positioned within the abdomen A.

At step 1210, optionally, the phototherapeutic light containment device can be advanced around the treatment end 22. For example, phototherapeutic light containment device 72 can be advanced until a distal end of the phototherapeutic light containment device contacts, e.g., a surface of the uterus surrounding the target tissue 93 (such as endometriosis).

At step 1212, the PDT can be delivered by applying the photosensitizer and the phototherapeutic light to a surface of the target tissue 93. For example, the phototherapeutic light can be generated by a light source to be emitted toward the target tissue 93 and contained by the phototherapeutic light. The light source can be attached to the surgical instrument. The light can additionally be light of a wavelength sufficient to activate the photosensitizer. The light from the light source can be passed through the therapy device including the surgical instrument. For example, the light can be emitted from light source 38 (FIG. 1), pass through light conductor 72 (FIG. 1) and into light emitter 24 (FIG. 1) of the treatment end 22.

At step 1214, the target tissue can be inspected to determine if more PDT needs to be applied to the target tissue or the patient can be inspected for additional target tissue that requires treatment. In particular, the therapy device 10 can be moved around within abdomen A to view different tissue. Steps 1212 and 1214 can be repeated 1216 as necessary to ensure that all target tissue has been removed from the patient. After it is determined that no additional tissue is to be removed, the patient can be prepared to end the procedure and close incision 91.

At step 1218, all instrumentation can be removed from the patient. For example, therapy device 10 can be removed from laparoscope 90 and laparoscope 90 can be removed from incision 91.

At step 1220, the incision can be closed. For example, incision 91 can be sutured or closed using any suitable means.

The benefits of the systems and methods of the present disclosure can be in the form of, for example, 1) combining photosensitizer and phototherapeutic light together at the tool-end of a surgical instrument to provide PDT capabilities at the tool-end of a surgical instrument, 2) eliminating the need to wait between the administration of a photosensitizer and when the phototherapeutic light is applied, 3) illuminating the need of guessing when there is a sufficient concentration of the photosensitizer at a desired target tissue, 3) providing targeted surface PDT therapy, 4) reducing times to perform surgical procedures, and 5) reducing the need for post-surgery pathology testing.

VARIOUS NOTES & EXAMPLES

Each of these non-limiting examples can stand on its own, or can be combined in various permutations or combinations with one or more of the other examples.

Example 1 provides a therapy device for providing photodynamic therapy to a target tissue, the therapy device comprising: an outer shaft extending from a proximal portion to a distal portion; a surgical instrument translatable within the outer shaft, the surgical instrument including: a treatment end located at the distal portion configured to apply a photosensitizer and deliver phototherapeutic light to the target tissue.

In Example 2, the subject matter of Example 1 optionally includes where the photosensitizer and the phototherapeutic light are simultaneously applied to a surface of the target tissue.

In Example 3, the subject matter of Examples 1-2 optionally includes where the surgical instrument includes a lighting system to provide the phototherapeutic light and an applicator system to deliver the photosensitizer.

In Example 4, the subject matter of Example 3 optionally includes where the lighting system includes a light source sufficient to generate a wavelength that matches an absorption peak of the photosensitizer.

In Example 5, the subject matter of Example 4 optionally includes where the lighting system further includes a light conductor coupled to the light source, the light conductor extending from the proximal portion to a light emitter located at the distal portion.

In Example 6, the subject matter of Example 5 optionally includes where the light emitter is connected to the light conductor to emit light from the light conductor toward the target tissue.

In Example 7, the subject matter of Example 6 optionally includes where the light source includes an optical fiber and the light emitter comprises an end surface of the optical fiber.

In Example 8, the subject matter of Example 3 optionally includes where the applicator system includes: an application shaft extending from the proximal portion to an applicator tip located at the distal portion, the application shaft defining a media conduit configured to deliver the photosensitizer from a media source to the application tip.

In Example 9, the subject matter of Example 8 optionally includes where the applicator system provides the photosensitizer to the target tissue in a predetermined form selected from one of: a stream, a spray, a paste, and a mist.

In Example 10, the subject matter of Example 9 optionally includes a generator coupled to the media source and the media conduit to deliver the photosensitizer from the media source, through the media conduit, and out the application tip in a desired form.

In Example 11, the subject matter of Example 10 optionally includes where the generator is an atomizer.

In Example 12, the subject matter of Examples 1-11 optionally includes a distension device configured to extend from the outer shaft and distend a body cavity.

In Example 13, the subject matter of Examples 1-12 optionally includes a phototherapeutic light containment device translatable within the outer shaft, the phototherapeutic light containment device configured to contain the phototherapeutic light to a specific location defined by the phototherapeutic light containment device.

In Example 14, the subject matter of Example 13 optionally includes where the phototherapeutic light containment device is formed from a material that does not transmit the phototherapeutic light.

In Example 15, the subject matter of Example 14 optionally includes where the phototherapeutic light containment device, when deployed from the outer shaft, is configured to surround the treatment end of the surgical device.

Example 16 provide a therapy device for providing photodynamic therapy to a target tissue, the therapy device comprising: a handle; a shaft extending from the handle at a proximal end to a distal end; a lighting system configured to apply a phototherapeutic light to a target tissue; and an application system configured to apply a photosensitizer to the target tissue.

In Example 17, the subject matter of Example 16 optionally includes where the lighting system includes: a light conductor extending from the handle and into the shaft; and a light emitter connected to the light conductor and configured to protrude from the distal end to illuminate the target tissue.

In Example 18, the subject matter of Examples 16-17 optionally includes where the application system includes: an application shaft extending from the handle and into the shaft, the application shaft defining a conduit; and an application tip defining an outlet configured to deliver the photosensitizer to the target tissue.

In Example 19, the subject matter of Examples 16-18 optionally includes where the shaft comprises: a tubular body having a wall defining a working lumen, the wall defining a gas-conduit configured to deliver oxygen to the target site.

In Example 20, the subject matter of Examples 16-19 optionally includes a distension device configured to extend from the outer shaft and distend a body cavity.

In Example 21, the subject matter of Examples 16-20 optionally includes a phototherapeutic light containment device translatable within the outer shaft, the phototherapeutic light containment device configured to contain the phototherapeutic light to a specific location defined by the phototherapeutic light containment device.

In Example 22, the subject matter of Examples 16-21 optionally includes a fallopian tube blocker configured to extend from the outer shaft and block an opening in fallopian tubes.

Example 23 provides a method for providing photodynamic therapy to a target tissue, the method comprising: delivering a photosensitizer and a phototherapeutic light to a surface of the target tissue to provide the photodynamic therapy to treat the target tissue.

In Example 24, the subject matter of Example 23 optionally includes where delivering a photosensitizer and a phototherapeutic light includes: simultaneously applying the photosensitizer and the phototherapeutic light to the surface of the target tissue.

In Example 25, the subject matter of Examples 23-24 optionally includes where delivering a photosensitizer and a phototherapeutic light includes: applying the photosensitizer to the surface of the target tissue; and applying, after a time period, applying the phototherapeutic light to the target tissue.

In Example 26, the subject matter of Example 25 optionally includes where the time period is less than 5 minutes.

In Example 27, the subject matter of Examples 25 optionally includes where the time period is less than 1 minutes.

In Example 28, the subject matter of Examples 25 optionally includes where the time period is less than 5 seconds.

In Example 29, the subject matter of Examples 23-28 optionally includes inserting a therapy device into the patient, the therapy device including an outer shaft extending from a proximal portion to a distal portion and surgical instrument translatable within the outer shaft and configured to provide the PDT.

In Example 30, the subject matter of Example 29 optionally includes where the surgical instrument includes: a lighting system to provide the phototherapeutic light; and an applicator system to deliver the photosensitizer.

In Example 31, the subject matter of Example 30 optionally includes where the applicator includes: an application shaft extending from the proximal portion to an applicator tip located at the distal portion, the application shaft defining a media conduit configured to deliver the photosensitizer from a media source to the application tip.

Example 32 provides a therapy device for providing photodynamic therapy to a target tissue, the therapy device comprising: a shaft including a proximal portion and a distal portion; a surgical instrument translatable within the outer shaft, the surgical instrument including a lighting system configured to apply phototherapeutic light to the target tissue and an applicator system configured to apply the photosensitizer to the target tissue.

In Example 33, the subject matter of Example 32 optionally includes where the applicator system includes: an expandable medium, near the distal portion of the shaft; a medium-delivery conduit, extending between the proximal portion and the distal portion of the shaft, the medium-delivery conduit comprising an outlet, near the distal portion of the shaft, for delivery of the medium toward the expandable medium; and a layer of the photosensitizer deposited onto an outer surface of the expandable medium.

In Example 34, the subject matter of Example 32 optionally includes where the applicator system includes: an expandable medium, near the distal portion of the shaft, the expandable medium including a first layer and a second layer, the second layer including pores; a medium-delivery conduit, extending between the proximal portion and the distal portion of the shaft, the medium-delivery conduit comprising a first outlet, near the distal portion of the shaft, for delivery of the medium toward the expandable medium; and a drug-delivery conduit, extending between the proximal portion and the distal portion of the shaft, the drug-delivery conduit comprising a second outlet, near the distal portion of the shaft, for delivery of the photosensitizer between the first layer and the second porous layer to deliver the photosensitizer to the target tissue.

In Example 35, the subject matter of Examples 32 optionally includes wherein the applicator system includes: an applicator shaft extending from the proximal portion and the distal portion of the shaft, wherein a light emitter, a light shaft, and a light conductor of the lighting system are positioned within the applicator shaft; a cover positioned at the distal end of the application shaft, the cover being transparent to the phototherapeutic light emitted by the light emitter; and a coating of the photosensitizer on an external surface of the cover.

In Example 36, includes the combination of any one of the Examples 1-35.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as The claimed invention is:

1. A therapy device for providing photodynamic therapy to a target tissue, the therapy device comprising:
   an outer shaft extending from a proximal portion to a distal portion; and
   a surgical instrument translatable within the outer shaft, the surgical instrument including:
      a treatment end located at the distal portion, the treatment end configured to advance from the outer shaft and configured to apply a photosensitizer and deliver phototherapeutic light to a treatment region including the target tissue, the treatment end including:
      a phototherapeutic light containment device surrounding the treatment end of the surgical instrument in an expanded configuration and configured to contain phototherapeutic light within the treatment region, the treatment region including the target tissue;
      wherein the phototherapeutic light containment device is configured to be advanced from the outer shaft and a distal end of the phototherapeutic light containment device is configured to contact at least a portion of a perimeter of the treatment region; and
      a distension device translatable within the outer shaft and configured to expand around the phototherapeutic light containment device.

2. The therapy device of claim 1, wherein the surgical instrument further includes:
   a lighting system to provide the phototherapeutic light; and
   an applicator system to deliver the photosensitizer;
      wherein at least a portion of the lighting system and at least a portion of the applicator system extends either within the outer shaft or extends along the outer shaft.

3. The therapy device of claim 2, wherein the lighting system includes a light source sufficient to generate a wavelength that matches an absorption peak of the photosensitizer.

4. The therapy device of claim 2, wherein the applicator system includes:
   an application shaft extending from the proximal portion to an applicator tip located at the distal portion, the application shaft defining a media conduit configured to deliver the photosensitizer from a media source to the applicator tip.

5. The therapy device of claim 4, further including:
   a generator coupled to the media source and the media conduit to deliver the photosensitizer from the media source, through the media conduit, and out the applicator tip in a predetermined form.

6. The therapy device of claim 5, wherein the generator is an atomizer.

7. The therapy device of claim 1, wherein, the distension device configured to extend from the outer shaft and distend a portion of a uterus.

8. The therapy device of claim 7, wherein the distension device surrounds at least a portion of the phototherapeutic light containment device.

9. The therapy device of claim 1, wherein the phototherapeutic light containment device is formed from a material that does not transmit the phototherapeutic light.

10. The therapy device of claim 1, wherein the phototherapeutic light containment device is configured to transition from a non-expanded position to an expanded position and the distal end of the phototherapeutic light containment device contacts an area around the target tissue.

11. The therapy device of claim 1 wherein the phototherapeutic light containment device is at least partially formed from a plurality of flexible members, each flexible member of the plurality of flexible members is connected to an adjacent flexible member with a flexible material.

12. The therapy device of claim 11, wherein the plurality of flexible members are configured to fluctuate in profile or dimension.

13. A therapy device for providing photodynamic therapy to a target tissue, the therapy device comprising:
   a handle;
   a shaft extending from the handle at a proximal end to a distal end;
   a lighting system configured to apply a phototherapeutic light to the target tissue;
   an application system configured to apply a photosensitizer to the target tissue;
   a distension member configured to distend a uterus; and
   a phototherapeutic light containment device configured to advance from within the shaft;
      wherein, when advanced from within the shaft, the phototherapeutic light containment device expands within an expanded distension device, the phototherapeutic light containment device surrounds the lighting system and the application system and a distal end of the phototherapeutic light containment device contacts a treatment area, the treatment area including the target tissue;
      wherein at least one of application of the phototherapeutic light or the photosensitizer is within the treatment area.

14. The therapy device of claim 13, wherein the lighting system includes:
   a light conductor extending from the handle and into the shaft; and
   a light emitter connected to the light conductor and configured to protrude from the distal end to illuminate the target tissue.

15. The therapy device of claim 13, wherein the application system includes:
   an application shaft extending from the handle and into the shaft, the application shaft defining a conduit; and
   an application tip defining an outlet configured to deliver the photosensitizer to the target tissue.

16. The therapy device of claim 13, wherein the phototherapeutic light containment device contains at least one of application of the phototherapeutic light or the photosensitizer within an area within a uterus.

17. A method for providing photodynamic therapy to a target tissue, the target tissue including intrauterine tissue, within a uterine cavity, the method comprising:
   inserting an outer shaft of a therapy device into the uterine cavity through a cervix;

expanding a phototherapeutic light containment device from the outer shaft;
surrounding the target tissue with the phototherapeutic light containment device within the uterine cavity;
extending a photosensitizer and a phototherapeutic light source within the phototherapeutic light containment device; and
delivering the photosensitizer and the phototherapeutic light within the phototherapeutic light containment device to a surface of the target tissue.

18. The method of claim 17, wherein delivering the photosensitizer and the phototherapeutic light includes:
simultaneously applying the photosensitizer and the phototherapeutic light to the surface of the target tissue.

19. The method of claim 17, wherein delivering the photosensitizer and the phototherapeutic light includes:
applying the photosensitizer to the surface of the target tissue; and
applying, after a time period, the phototherapeutic light to the target tissue.

20. The method of claim 19, wherein the time period is less than 5 minutes.

21. The method of claim 19, wherein the time period is less than 1 minute.

22. The method of claim 17, further includes:
inserting a therapy device into a patient, the therapy device including:
an outer shaft extending from a proximal portion to a distal portion; and
a surgical instrument translatable within the outer shaft and configured to provide the photodynamic therapy;
wherein the surgical instrument, the phototherapeutic light containment device, and a distention member are inserted into the uterine cavity;
wherein the phototherapeutic light containment device is configured to contain the photosensitizer and the phototherapeutic light to the intrauterine tissue.

23. The method of claim 22, wherein the surgical instrument includes:
a lighting system to provide the phototherapeutic light; and
an applicator system to deliver the photosensitizer.

24. The method of claim 23, wherein the applicator system includes:
an application shaft extending from the proximal portion to an applicator tip located at the distal portion, the application shaft defining a media conduit configured to deliver the photosensitizer from a media source to the applicator tip.

25. The method for providing the photodynamic therapy of claim 17, further comprising:
inserting a distention member into the uterine cavity; and
surrounding the phototherapeutic light containment device with the distention memeber.

* * * * *